United States Patent
Leonhard et al.

(10) Patent No.: US 8,956,645 B2
(45) Date of Patent: Feb. 17, 2015

(54) WATER-SOLUBLE PHARMACEUTICAL COMPOSITION COMPRISING AT LEAST ONE THERAPEUTICALLY ACTIVE SUBSTANCE HAVING HYDROPHOBIC PROPERTIES AND AT LEAST ONE COMPOUND SELECTED FROM AMONG SIALOGLYCOSPHINGOLIPIDS, GLYCOSPHINGOLIPIDS OR A MIXTURE OF SIALOGLYCOSPHINGOLIPIDS AND GLYCOSPHINGOLIPIDS

(75) Inventors: Victoria Leonhard, Córdoba (AR); Valeria Alasino, Córdoba (AR); Ismael Bianco, Córdoba (AR); Dante Beltramo, Alicante (ES)

(73) Assignees: Consejo Nacional de Investigaciones Cientificas y Tecnicas (Conicet), Buenos Aires (AR); Centro de Excelencia en Productos y Procesos de Cordoba (Ceprocor), Cordoba (AR)

( * ) Notice: Subject to any disclaimer, the term of this patent is extended or adjusted under 35 U.S.C. 154(b) by 0 days.

(21) Appl. No.: 13/635,595

(22) PCT Filed: Mar. 14, 2011

(86) PCT No.: PCT/ES2011/070174
§ 371 (c)(1),
(2), (4) Date: Dec. 27, 2012

(87) PCT Pub. No.: WO2011/113981
PCT Pub. Date: Sep. 22, 2011

(65) Prior Publication Data
US 2013/0195924 A1  Aug. 1, 2013

(30) Foreign Application Priority Data

Mar. 17, 2010 (AR) .............................. P20100100854

(51) Int. Cl.
| | |
|---|---|
| A61K 9/127 | (2006.01) |
| A61K 47/26 | (2006.01) |
| A61K 8/02 | (2006.01) |
| A61K 9/00 | (2006.01) |
| A61K 9/107 | (2006.01) |
| A61K 31/337 | (2006.01) |
| A61K 31/704 | (2006.01) |
| A61K 31/7048 | (2006.01) |
| A61K 38/38 | (2006.01) |

(52) U.S. Cl.
CPC ............... *A61K 47/26* (2013.01); *A61K 8/0291* (2013.01); *A61K 9/0019* (2013.01); *A61K 9/1075* (2013.01); *A61K 31/337* (2013.01); *A61K 31/704* (2013.01); *A61K 31/7048* (2013.01); *A61K 38/38* (2013.01)
USPC ......................................................... 424/450

(58) Field of Classification Search
None
See application file for complete search history.

(56) References Cited

U.S. PATENT DOCUMENTS

| | | | |
|---|---|---|---|
| 5,637,569 A * | 6/1997 | Magnusson et al. | ............ 514/25 |
| 2007/0082855 A1 | 4/2007 | Veldman et al. | |
| 2010/0266491 A1* | 10/2010 | Farokhzad et al. | .......... 424/1.29 |

FOREIGN PATENT DOCUMENTS

| | | |
|---|---|---|
| CN | 101439020 | 5/2009 |
| CN | 101439032 | 5/2009 |
| CN | 101439033 | 5/2009 |
| EP | 1655038 | 5/2006 |
| EP | 1980243 | 10/2008 |
| JP | 8034746 | 2/1996 |
| WO | WO 2006/068890 | 6/2006 |
| WO | WO 2008133597 A1 * | 11/2008 |

OTHER PUBLICATIONS

International Search Report for PCT/ES2011/070174 mailed Jul. 27, 2011.

* cited by examiner

*Primary Examiner* — Susan Tran
(74) *Attorney, Agent, or Firm* — RatnerPrestia

(57) ABSTRACT

This invention discloses water soluble pharmaceutical compositions including at least one therapeutically active substance and at least one compound selected from the sialoglycosphingolipids, the glycosphingolipids or a mixture of sialoglicosphingolipids and glycosphingolipids, in which at least one of the therapeutically active substances is a drug with hydrophobic characteristics. In particular, sterile compositions for i.v. administration, composed of nano-glycosphingolipids micelles or modified glycosphingolipids, which can be coated with albumin in a noncovalent form and which allow transport and controlled release of highly hydrophobic molecules are disclosed.

22 Claims, 15 Drawing Sheets

FIGURE 1

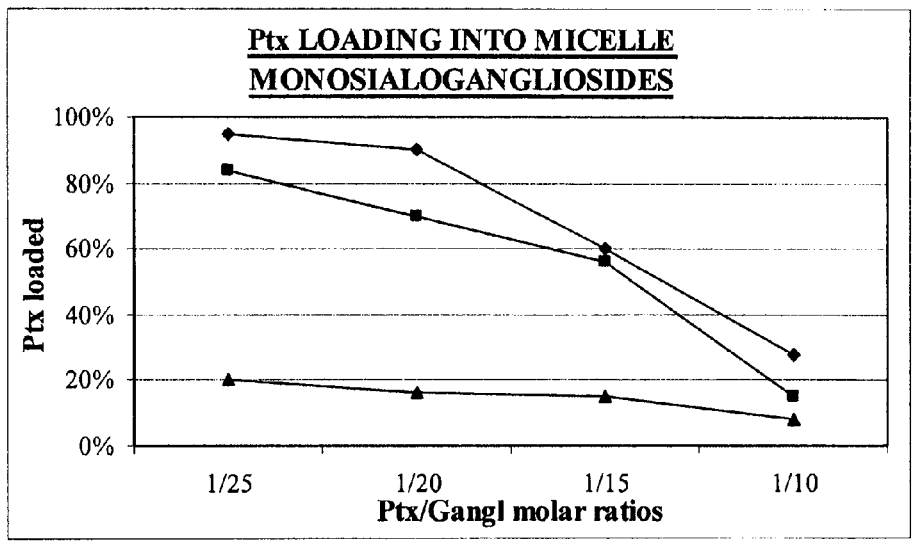

Figure 4:
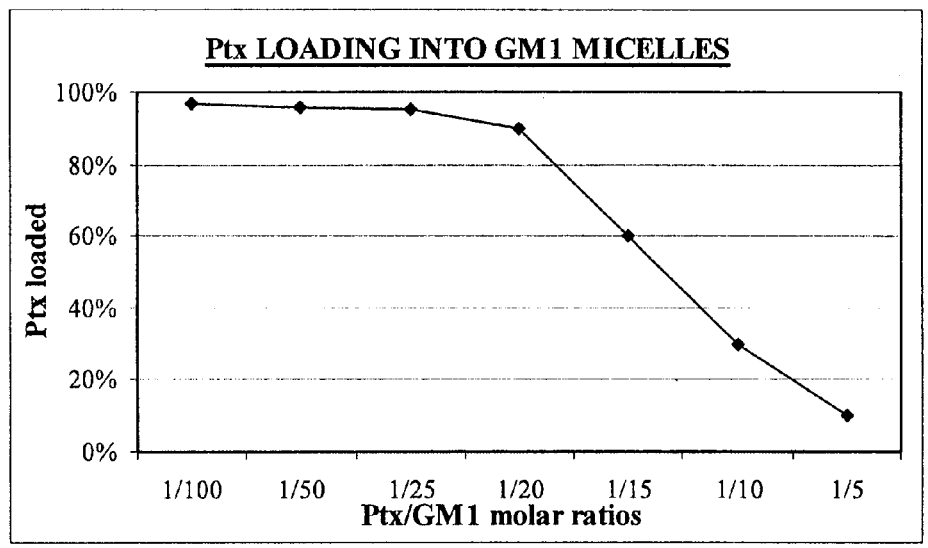

Samples of monosialoganglioside GM1 (—♦—), GM2 (—■—) and GM3 (—▲—) containing 100 mg were dissolved in 1 ml of water distilled with pH 5, or 1 ml of buffer acetic-acetate 20 mM pH 5 with gentle agitation until complete dissolved. This solution is allowed to stand for at least 24 hours at 4 or 8 °C. Transparent solution was then centrifuged at 50,000 xg for 15 minutes and the supernatant was filtered through 0.22 μm pore.

Aliquots of 0.5 ml of each monosialoganglioside of 100 mg/ml solution were incubated with 50 μl of DMSO containing an increasing amount of Ptx in order to achieve the following Ptx-ganglioside molar ratios: 1/25, 1/20, 1/15 to 1/10. Solutions were incubated at 4 °C for an hour and then centrifuged at 15,000 xg for 15 min to remove insoluble Ptx that had not been encapsulated into the micelles. Finally, samples are dialyzed in distilled water or acetic-acetate 20 mM pH 5 solution for 24 hours in order to remove all DMSO. Ptx quantification was carried out by HPLC.

FIGURE 2

CHROMATOGRAPHIC PROFILE OF THE INTERACTION BETWEEN GM1 AND Ptx

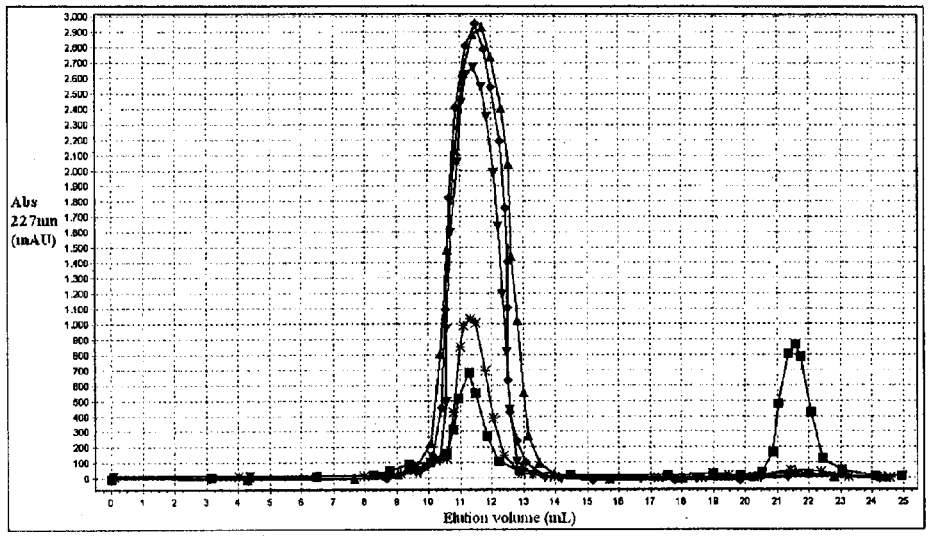

Samples of GM1 monosialoganglioside with 100 mg were dissolved in 1 ml of distilled water with pH 5, or 1 ml of buffer acetic-acetate 20 mM pH 5 solution with gentle agitation until completely dissolved. This solution is allowed to stand for at least 24 hours at 4 or 8 °C. The transparent solution was then centrifuged at 50,000 xg for 15 minutes and the supernatant was filtered by 0.22 µm pore.

Aliquots of 0.5 ml of 100 mg/ml were incubated with 50 µl of DMSO containing an increasing amount of Ptx to achieve the following Ptx-GM1 ratios: 1/100, 1/50, 1/25 to 1/11. The solutions were incubated at 4 °C for an hour and then centrifuged at 15,000 xg for 1 minute to remove the insoluble Ptx material that had not been encapsulated into GM1 micelles. Finally, the samples are dialyzed with distilled water or acetic-acetate 20 mM pH 5 solution for 24 hours in order to remove all DMSO.

An aliquot of each 400ul sample is injected into a filtration AKTA Explorer molecular system using a G200 Sephadex column and a running buffer phosphate pH 7 50 mM NaCl 150 mM.

The following molecular weights were identified:

GM1 (-■-) ☐ 365 KDa (micelles) and 1.6KDa (monomers)

Ptx/GM1: 1/100 (-✳-) → 350 KDa

Ptx/GM1: 1/50 (-▼-) → 315 KDa

Ptx/GM1: 1/25 (-♦-) → 280 KDa

Ptx/GM1: 1/11 (-▲-) → 255 KDa

FIGURE 3

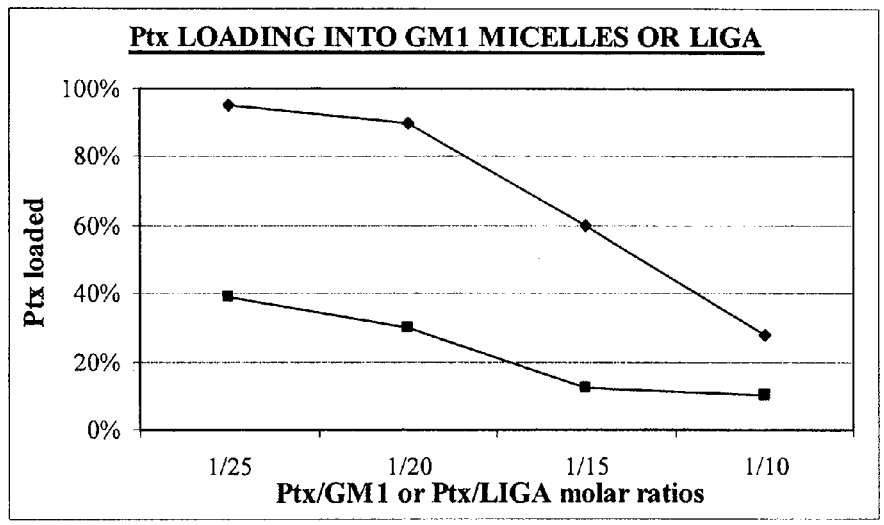

Samples of GM1 (—♦—) and LIGA (—■—) with 100 mg were dissolved in 1 ml of distilled water with pH 5, or 1 ml of buffer acetic-acetate 20 mM pH 5 solution with gentle agitation until completely dissolved. This solution is allowed to stand for at least 24 hours at 4 or 8 °C. The transparent solution was then centrifuged at 50,000 xg for 15 minutes and the supernatant was filtered through 0.22 μm pore.

Aliquots of 0.5 ml of 100 mg/ml of each solution were incubated with 50 μl of DMSO containing an increasing amount of Ptx to achieve the following ratios Ptx-GM1 or Ptx-LIGA: 1/25, 1/20, 1/15 to 1/10. The solutions were incubated at 4 °C for an hour and then centrifuged at 15,000 xg for 15 min to remove the Ptx insoluble material that had not been encapsulated into GM1 micelles. Finally the samples are dialyzed with distilled water or solution of acetic-acetate 20 mM pH 5 by 24 hours in order to remove the DMSO. Ptx determination associated to the micelles is determined by HPLC.

GM1 solutions were incubated with an increasing amount of Ptx to achieve following Ptx-GM1 molar ratios: 1/100, 1/50, 1/25, 1/20, 1/15, 1/10 and 1/5.

Quantification of Ptx incorporated into GM1 micelles was carried out by HPLC.

Paclitaxel is loaded into the ganglioside micelles in ratios: 1/10, 1/15, 1/20, 1/25. The loading is performed for 30 minutes at A-(▨) 0°C, B-(▢) GM1 preheated at 55 °C and Ptx load at 0°C, C-(▩) GM1 preheated at 55 °C and Ptx load at 25 ° C, and D-(▨) GM1 preheated and loaded at 55 °C.

The amount of Ptx incorporated, in a soluble form, into GM1 micelle was quantified by HPLC.

Non tumoral VERO and MA cells were incubated with increasing concentrations of a)- (—▲—) Ptx in DMSO, b)- (—✕—) Ptx-GM1 micelles 1/25, c)- (—■—) GM1 micelles and d)- (—◆—) albumin-Ptx-GM1 complex micelles.

Cell viability was assessed using MTT assay after 24 hours of incubation.

HEP-2 and HELA tumoral cells were incubated with increasing concentrations of a)- (—▲—) Ptx in DMSO, b)- (—✕—) Ptx - GM1 1/25 micelles, c)- (—■—) GM1 micelles and d)- (—◆—)albumin-Ptx-GM1 complex micelles.

Cell viability was assessed using MTT assay after 24 hours of incubation.

GM1 samples (—◆—) and Ptx-GM1: 1/25 complex (—■—) were incubated with increasing concentrations of doxorubicin in order to reach Dox-GM1 complex molar ratios: 1/10, 1/5, 1/ 2.5 and 1/1.

Quantification of Doxo incorporated into the micelles was carried out by spectrophotometry at 492 nm.

CHROMATOGRAPHIC PROFILE OF THE GM1 AND ALB INTERACTION

FIGURE 9A

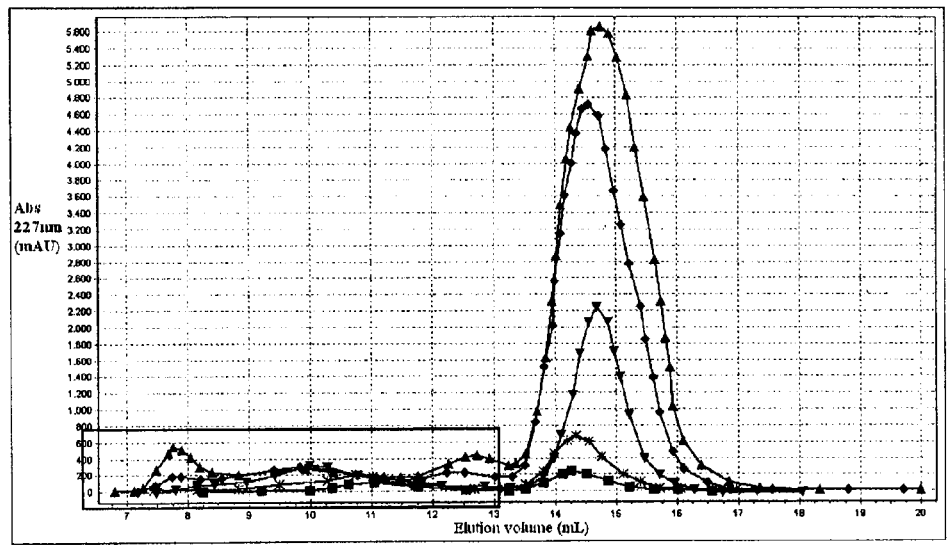

FIGURE 9B

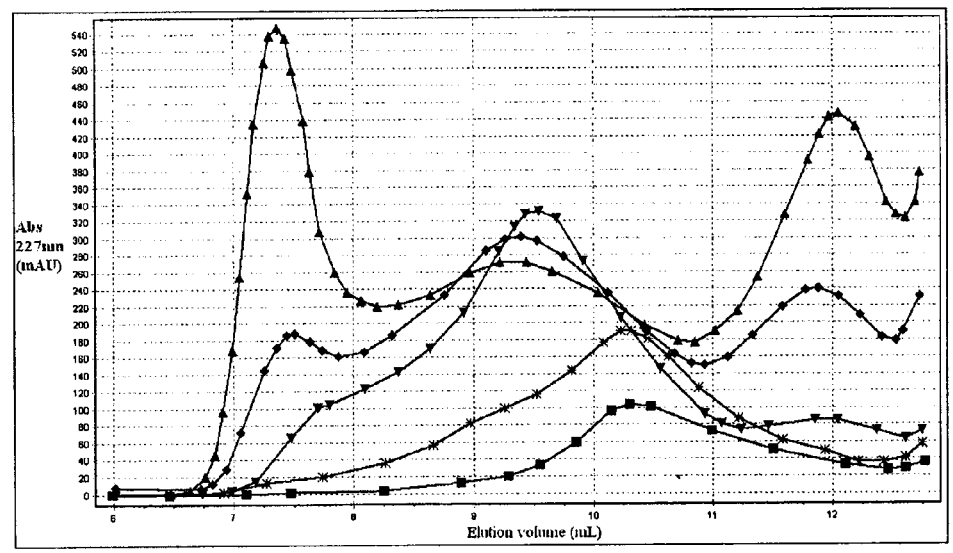

GM1 micelles with 5 mg/ml of GM1 were incubated with increasing amounts of purified human serum albumin in order to reach the following concentrations: 0.83, 1.67, 5, 15 and 30 mg/ml final concentration that represent GM1-Alb ratios (w/w): 6/1 (-■-), 3/1 (-✳-), 1/1 (-▼-), 1/3 (-◆-) and 1/6 (-▲-), respectively.

The incubations were performed at 37 °C for 3 hours.

Figure A corresponds to all the chromatographic run, while B represents the insert pointed out in A, corresponding to the peaks obtained at higher MW.

CHROMATOGRAPHIC PROFILE OF THE Ptx-GM1 INTERACTION: 1/25 WITH ALB

FIGURE 10A

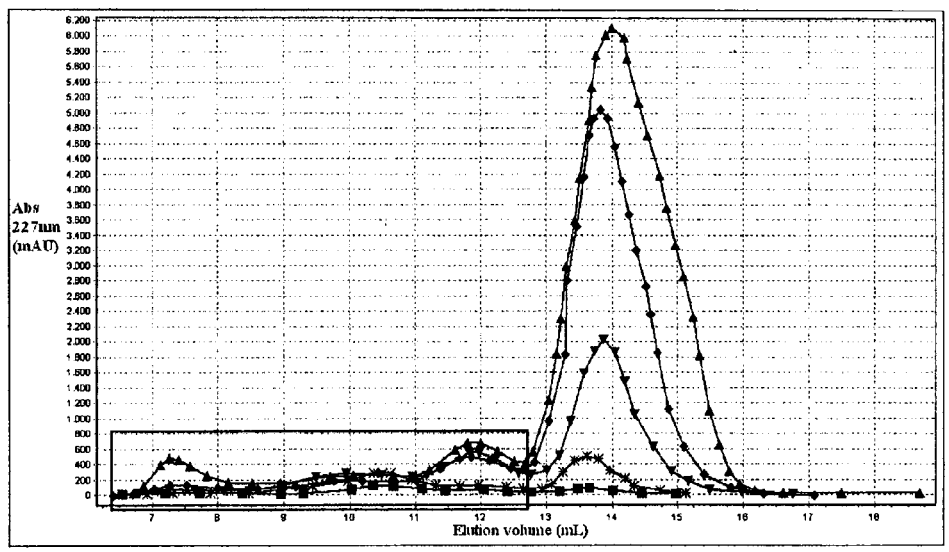

FIGURE 10B

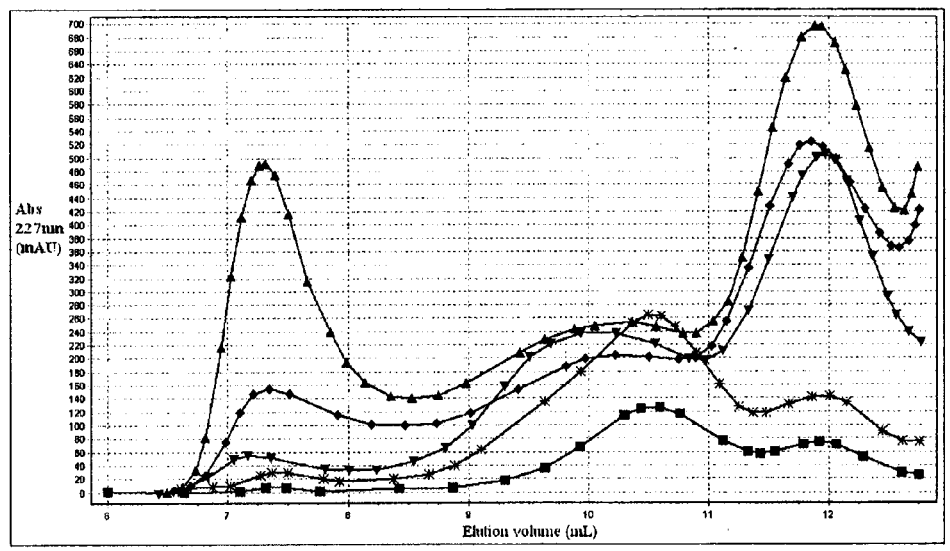

Ptx-GM1 Micelles with 5 mg/ml of GM1 and a Ptx-GM1 molar ratio: 1/25 were incubated with increasing amounts of purified human serum albumin in order to reach the following concentrations: 0.83, 1.67, 5, 15 and 30 mg/ml final concentration that represent GM1-Alb ratios (w/w): 6/1 (-■-), 3/1 (-✱-), 1/1 (-▼-), 1/3 (-◆-) and 1/6 (-▲-), respectively. Incubations were performed at 37 °C for 3 hours.

Figure A corresponds to all the chromatographic run, while B represents the insert pointed out in A, corresponding to the peaks obtained at higher MW.

CHROMATOGRAPHIC PROFILE OF THE INTERACTION OF Ptx-GM1: 1/25 WITH ALB AT 4 °C

FIGURE 11A

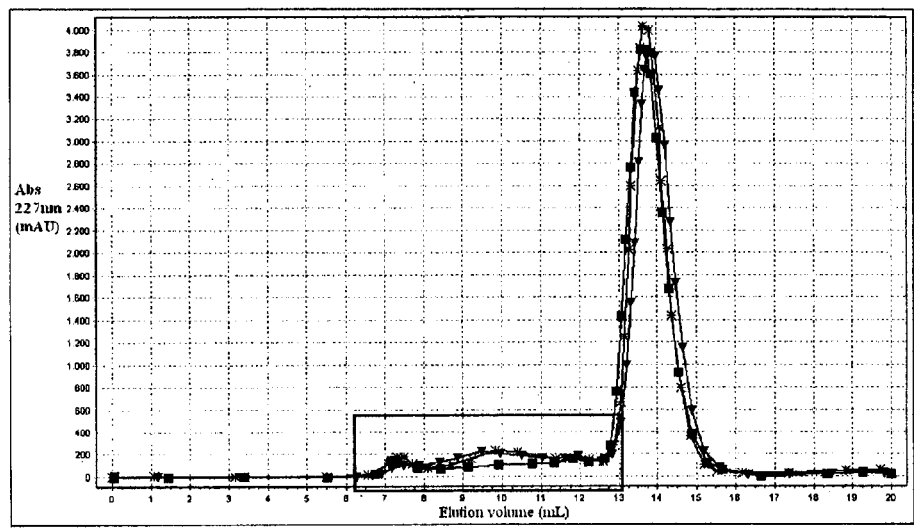

FIGURE 11B

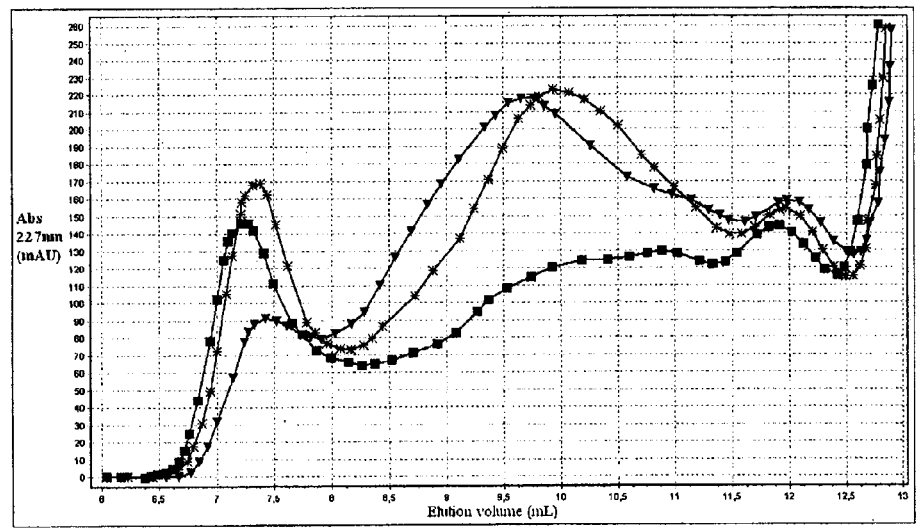

Ptx-GM1 micelles with a Ptx-GM1: 1/25 molar ratio were incubated with a fixed concentration of purified human serum albumin in order to reach the GM1-Alb 1/1 (w/w) ratio at 4 °C for 1h (-■-), 4hs (-*-) and 24hs (-▼-).

Figure A corresponds to all the chromatographic run, while B represents the insert pointed out in A, corresponding to the peaks obtained at higher MW.

CHROMATOGRAPHIC PROFILE OF THE INTERACTION OF Ptx-GM1: 1/25 WITH ALB AT 37 °C

FIGURE 12A

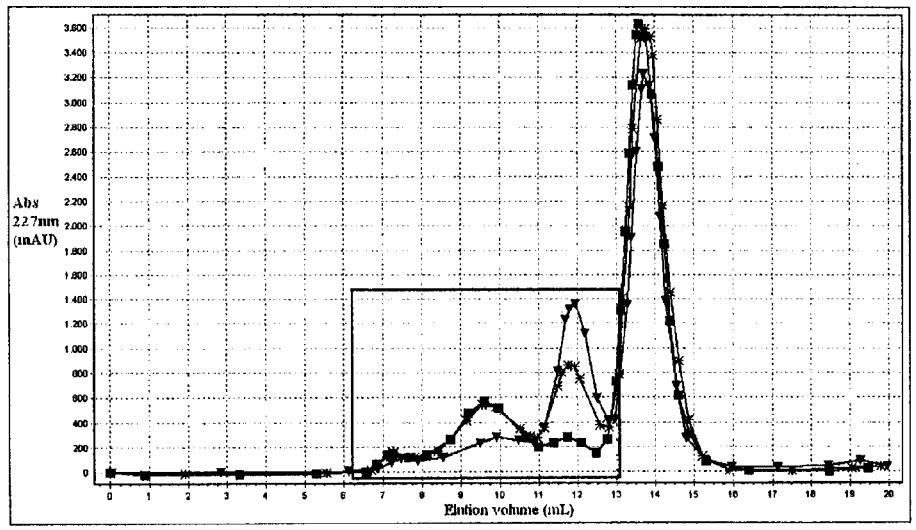

FIGURE 12B

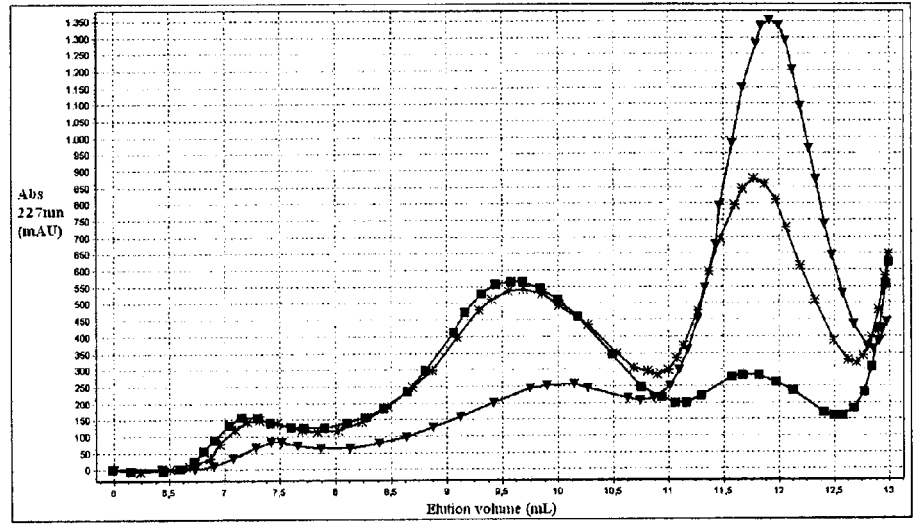

Ptx-GM1 micelles with a Ptx-GM1: 1/25 molar ratio were incubated with a fixed concentration of purified human serum albumin in order to reach the GM1-Alb 1/1 w/w ratio at 37 °C for 1h (-■-), 4hs (-✱-) and 24hs (-▼-).

Figure A corresponds to all the chromatographic run, while B represents the insert pointed out in A, corresponding to the peaks obtained at higher MW.

FIGURE 13

CHROMATOGRAPHIC PROFILE OF THE INTERACTION OF Ptx-GM1: 1/25 WITH ALB AT 55 °C

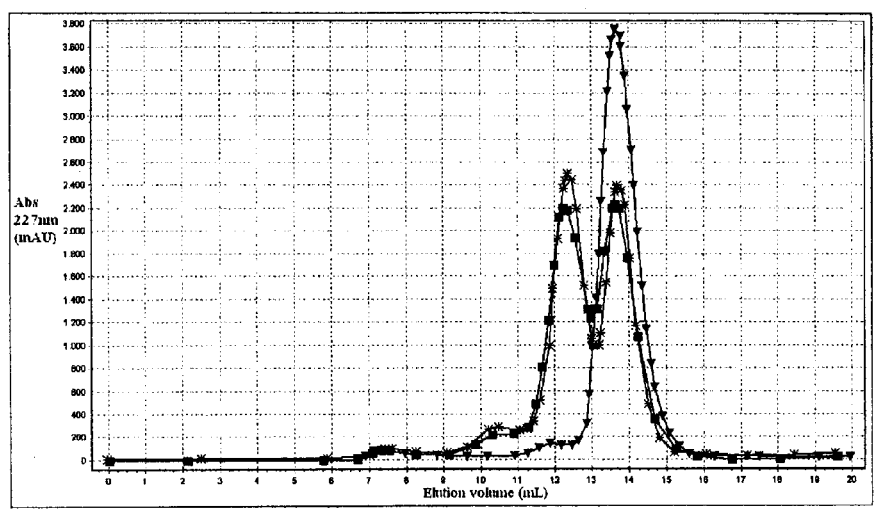

Ptx-GM1 micelles with a Ptx-GM1: 1/25 molar ratio were incubated with a fixed concentration of purified human serum albumin in order to reach the GM1-Alb 1/1 w/w ratio at 55 °C for 1h (-■-) and 4hs (-*-).

Also included in the figure is a sample of albumin (-▼-) incubated for 4 hs at 55 °C as control of the protein stability at this temperature.

FIGURE 14

ABSORPTION SPECTRA OF GM1-AmB COMPLEXES

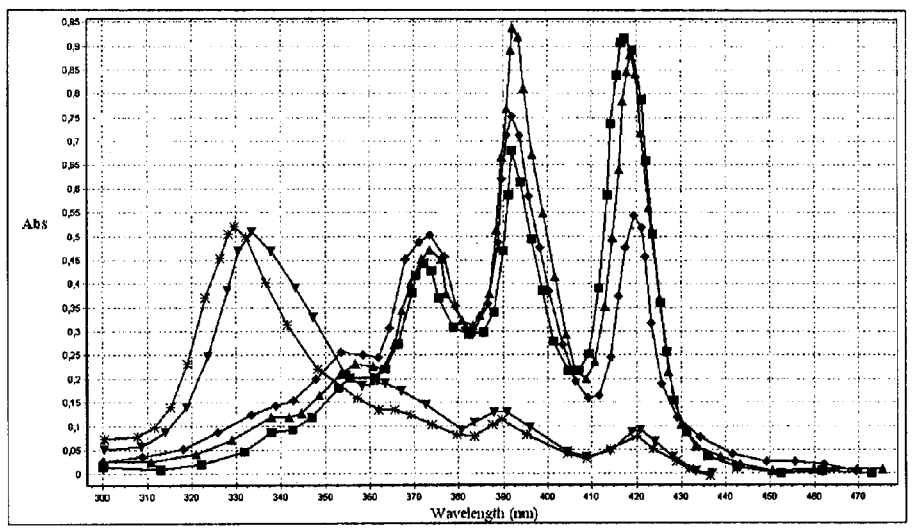

GM1 solutions were incubated with AmB in order to reach a final GM1/AMB molar ratio of 1/5 (-✳-), 1/1 (-▼-), 5/1 (-♦-) and 25/1 (-▲-).

A spectral curve of each sample from 300 to 500 nm is drawn.

In the figure, there is also a sample AmB in ethanol (-■-) as control of the monomeric state which the AmB adopts.

Samples 1/5 and 1/1 adopt an aggregate form that presents an absorption maximum at 345 nm; while 5/1 and 25/1 samples adopt a monomeric form with maximum absorption peaks at 365, 385 and 410 nm.

FIGURE 15

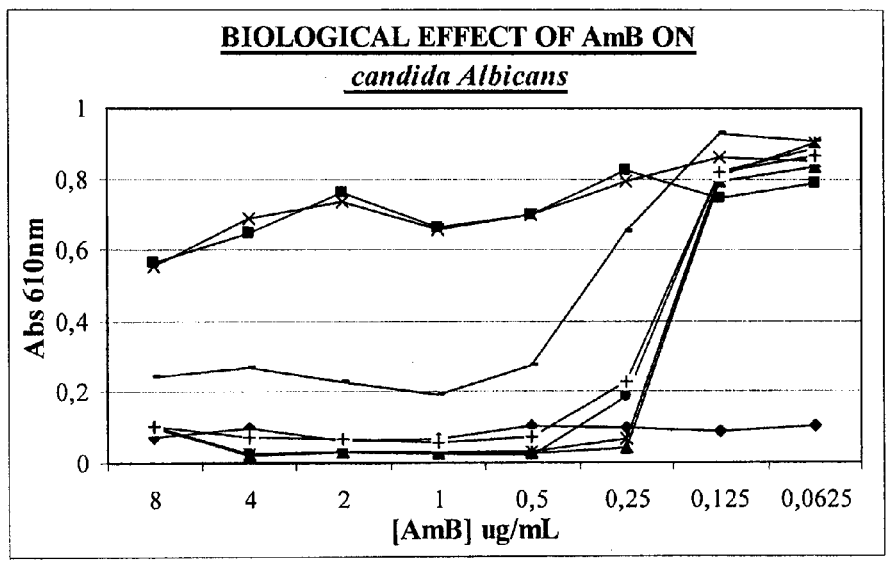

AmB-GM1 micelles with molar ratios between 5/1 (—♦—), 2.5/1 (—●—), 1/1 (—+—) and 1/2.5 (—*—) were prepared using a fixed concentration of AmB 16 ug/ml. A GM1 micelle control (—□—), and an AMB (—▲—) control were prepared to assess the effect of each in a separate manner, as well as a positive control (—■—) and a negative (—♦—) for the micro-organism growth.

The different GM1-AmB preparations and their respective controls were incubated with a *candida Albicans* solution at a concentration of $1 \times 10^5$ cells/ml on a 96 well plate for 24 hours at 37 °C. Serial dilutions were performed on the plate until a final AmB concentration of 0.0625 ug/ml was reached. After incubation, the turbidity of the solution, which represents the micro-organism growth, was evaluated by spectrophotometry at 610nm.

WATER-SOLUBLE PHARMACEUTICAL COMPOSITION COMPRISING AT LEAST ONE THERAPEUTICALLY ACTIVE SUBSTANCE HAVING HYDROPHOBIC PROPERTIES AND AT LEAST ONE COMPOUND SELECTED FROM AMONG SIALOGLYCOSPHINGOLIPIDS, GLYCOSPHINGOLIPIDS OR A MIXTURE OF SIALOGLYCOSPHINGOLIPIDS AND GLYCOSPHINGOLIPIDS

This application is the U.S. national phase of International Application No. PCT/ES2011/070174 filed 14 Mar. 2011 which designated the U.S. and claims priority to AR P20100100854 filed 17 Mar. 2010, the entire contents of each of which are hereby incorporated by reference.

STATE OF THE ART

The efficacy of many drugs, especially those with hydrophobic characteristics, is limited mainly by its lack of ability to reach the right site for therapeutical action. In many instances, and even when the drug is water soluble, only a small fraction of the administered dose reaches its therapeutical site while most of the drug is distributed all over the body. Thus, this distribution in healthy organs and tissues frequently limits its dose. Therefore, an ideal pharmaceutical formula—that having highly hydrophobic active principles—would be one which allows for a great solubility of the drug in a water medium, that which is stable as a complex without dissolution and that, at the same time, concentrates on the specific activity site.

Among the active principles having a hydrophobic nature and very low or limited water solubility, those used in oncological treatment (Paclitaxel, Docetaxel and Doxorrubicine, for example), anti mycosis (Anfotericina B, for example), hormones (Progesterone) and the anaesthetics (Propofol, for example) can be mentioned as examples. Also included are prostaglandines, Isosorbide dinitrate, Testosterone, Nitroglycerine, Estradiol, vitamin E, Cortisone, Dexametasone and its esters, and Betametasone Valerate.

In particular, paclitaxel (Ptx) is a diterpene compound with anti cancer properties isolated from the *Taxus brevifolia* tree. Its use for cancer treatment was proposed after a raw extract of the above mentioned tree proved to have antineoplasic activity during a pre clinic study carried out by the National Cancer Institute in the United States of America about 30 years ago.

Ptx is a molecule that interacts and promotes polymerization of tobuline to form highly stable microtubules. This MT stabilization results in the inhibition of the normal dynamics of the reorganization of the microtubular net. This is the opposite to what happens with other antimicrotubular agents such as colchicine, vincristine or vinblastine, for example, which produce disassembly of the MT. (other antimicrotubular agents such as colchicine, vincristine or vinblastine, for example, show the opposite behaviour: they produce disassembly of the MT)

One of the major difficulties found in the development of medicines having PTX has been its great inability to dissolve in water. Drug formulations with low water solubility have traditionally been elaborated as emulsions or associating the drug with colloids, such as micelles, which dissolve the drug and, therefore, increase their concentration in an aqueous medium. Specifically, PTX has very low water solubility (less than 10 µg/ml); therefore, different carriers have been studied for intravenous infusion. In fact, certain organic solvents are able to partially dissolve PTX; however, when a miscible solvent is diluted in an aqua medium with the water it contains and in which Ptx is near its saturation point, the drug starts to precipitate.

Due to this, for administration of the drug in humans, in the different clinical trials, different Ptx compositions using 50% Cremofor EL/50% dehydrated alcohol, diluted either in physiological solution or in dextrose 5% in water up to a final concentration of Cremofor EL and of dehydrated alcohol 5% or less were formulated.

At present, Ptx injection is marketed worldwide by Bristol-Myers Squibb Co. (New York, N.Y.) in one 30 mg (5 ml) dose.

Each millimeter of the formulation contains about 6 mg of Ptx, 527 mg of Cremofor EL, and 49.7% (vol/vol) of dehydrated alcohol. For administration, this concentrated formulation can be diluted in physiological solution, 5% dextrose in water, 5% dextrose in physiological solution or Ringer solution with 5% dextrose in water (Goldspiel, 1994, "Pharmaceutical Issues: Preparation, Administration, Stability, and Compatibility with Other Medications" Ann. Pharmacotherapy, vol. 28, pp. S23-26. Harvey Whitney Books Company). However, it should be noted that Ptx formulation in Cremophore/ethanol when diluted in an aqueous medium becomes unstable, and fibrous precipitates start to appear. Ptx formulations in Cremophore can be seen in U.S. Pat. No. 5,504,102 patent.

Like most chemotherapeutic agents, the maximum tolerated dose is limited by its toxicity. In humans, most Ptx toxic effects can be observed in concentrations ranging from about 100 up to about 250 mg/m2. For example, among the adverse effects, the literature mentions granulocytopenia, (Holmes F. A. et al., "Phase II trial of taxol, an active drug in the treatment of metastatic breast cancer", *J Natl Cancer Inst.* 1991, 83:1797-1805), and systemic peripheral neuropathy, the latter being the main non haematological toxicity (Rowinsky E. K. et al., 1995, Review Article. Drug Therapy—Paclitaxel (Taxol) N. Engl. J. Med. Vol 332:1004-1014 N.15).

Recently, Ptx has been prepared in a liquid state for parenteral infusion and in a solid state. U.S. Pat. No. 6,743, 826 patent describes a method to obtain soluble Ptx by interaction with human albumin or recombinant human albumin. On the other hand, US 2005282734 A1 patent describes a lyophilized formulation or a water soluble composition containing Ptx or Docetaxel combined with human albumin in which Ptx concentration is higher than 500 ug/ml. However, said application does not clearly show the Ptx solubility in the formulation.

Albumin molecule plays a key roll in the delivery of hydrophobic molecules such as Ptx. Its accumulation in the different tissues is related to the ability of the albumin to interact with the cell receptors (Gradishar W. J., 2006, "Albumin-bound paclitaxel: A next-generation taxane, Expert Opin Pharmacother; 7:1041-1053).

By binding to the receptor, albumin starts what is called transcytosis of the albumin-Ptx complex through the walls of the blood vessel endothelial cells enabling the passage of the albumin-Ptx complex (called ABI-007) to the interstitial complex and, therefore, permitting its direct exposure to the tumour surface (Ibrahim N. K. et al., 2002, "Phase I and pharmacokinetic study of ABI-007, a Cremophor-free, protein-stabilized, nanoparticle formulation of paclitaxel", Clin Cancer Res-; 8:1038-1044; Gradishar W. J., 2006, "Albumin-bound paclitaxel: A next-generation taxane", Expert Opin Pharmacother, 7:1041-1053; Drummond D. C. et al., 1999, "Optimizing liposomes for delivery of chemotherapeutic agents to solid tumors". Pharmacol Rev.; 51:691-743).

Albumin accumulates in the tumours, at least in part, as a result of the secretion of the so called albumin binding protein (SPARC, secreted protein, acidic and rich in cysteine, also called BM-40) which may result in albumin bound Ptx intra-tumor accumulation (Fukunaga-Kalabis M. and Herlyn M., 2007, "Unraveling mysteries of the multifunctional protein SPARC", J Invest Dermatol; 127:2497-2498). On the other hand, other strategies to obtain water soluble Ptx have been recently published in the specialized literature such as binding it to polyglutamic polymers, for example (U.S. Pat. No. 7,384,977).

On the other hand, amphotericin B (AmB), a polienic antibiotic, is another highly hydrophobic molecule. This molecule acts mainly by interaction with sterols, such as ergostrol found in fungal membranes, increasing permeability. Nevertheless, the use of amphotericin B for treatment of systemic fungal infections is strongly associated with extensive renal damage. (Bennet J. E., 1996 "Antimicrobial agents". In: Hardman J G, Limbird L E, Molinoff P B, Ruddon R W, Goodman Gilman A, editors. Goodman and Gilman's The Pharmacological Basis of Therapeutics. 9th ed. New York: McGraw Hill,: 1175-90.) Probably, the toxicity observed in humans could be associated with the fact that it interacts with the cholesterol in the cells of all mammals.

To solve these problems, AmB was initially prepared in a micellar formulation, which was approved by FDA and marketed under the name of Anfostat. Later, a liposomal formulation of amphotericin B, marketed as Ambisome, was developed (Boswell G. W. et al., 1998, "AmBisome (Liposomal amphotericin B): A comparative review", J Clin Pharmacol vol. 38:583-92). This product was the first liposomal formulation to be approved for clinical use for the treatment of systemic fungal infections, (Gray A. and Morgan J. (1991) Liposomes in hematology. Blood Rev; 258-271).

Liposomal amphotericin B at normal doses is characterized by preferential delivery to the liver and spleen, thus reducing renal toxicity characteristic of amphotericin B (Boswell G. W. et al., 1998, "AmBisome (Liposomal amphotericin B): A comparative review", J Clin Pharmacol vol. 38:583-92; Ahmad I. et al., 1991, "Tissue distribution and antileishmanial activity of liposomised amphotericin-B in BALB/c mice". J Biosci. vol 16:217-21). however, when used at high doses, renal toxicity reappears (Longuet P. et al., 1991, "Limited protection by small unilamellar liposomes against the renal tubular toxicity induced by repeated amphotericin B infusion in rats". Antimicrob Agent Chemother; vol. 35:1303-1308). Apparently, this toxicity could be due to the saturation of the uptake mechanism of liver and spleen macrophages.

Ambisome can also be used for the treatment of parasitic drug-resistant infections of the reticuloendothelial system (Davidson R. N. et al., 1991, "Liposomal amphotericin B in drug-resistant leishmaniasis"; Lancet vol. 337:1061-1062). In fact, the ability of the liposomes to be captured by the macrophages and to concentrate in the liver and spleen makes them ideal for treatment of liver and kidney diseases, such as leishmaniasis.

Besides, it is interesting to notice that liposomes can also be directed to the lungs when coated with 0-stearoyl amilopectine and polioxiethylene or monosialogangliosides. (Deol P, Khuller G K. (1997) "Lung specific stealth liposomes: stability, biodistribution and toxicity of liposomal antitubercular drugs". Biochim Biophys Acta vol. 1334:161-72).

The encapsulation of liposomes anti-tuberculosis agents such as rifampicine or isoniazid modulates or regulates their toxicity (Deol P. and Khuller G. K., 1997, "Lung specific stealth liposomes: stability, biodistribution and toxicity of liposomal antitubercular drugs", Biochim Biophys Acta vol. 1334:161-72) and improve the efficacy of these drugs (Deol P. et al., 1997, "Therapeutic efficacies of isoniazid and rifampin encapsulated in lung-specific stealth liposomes against Mycobacterium tuberculosis infection induced in mice". Antimicrob Agent Chemother vol. 41:1211-4). Conventional liposomes have been formulated to carry drugs or other active agents in the aqueous phase of their core (hydrophilic drugs) or partitioned in the lipid bilayer (non hydrophilic drugs). Encapsulation of various antitumor $\bigcirc$ antimicotic drugs in conventional liposomes has been proved to diminish the cytotoxic side-effects produced by the drug, thus maintaining or, in some cases, increasing the desired antitumor or therapeutic effect. This decrease in the toxicity comes as a result of liposome ability to decrease exposure to the drug and the consequent damage to the undesirable tissue.

The mechanism whereby encapsulated anticancer or antifungal drugs actuate is not yet clearly understood; it could be the result of either the liposome ability to release an encapsulated drug slowly into the blood circulation, or of the liposome interaction with tumour surface to release the drug slowly into the target tumour. However, liposome-encapsulated drugs pose a serious problem: they have been found to be rapidly released from the liposomes after encapsulation. Furthermore, strongly lipophilic (water-insoluble) drugs that partition in the liposome lipid bilayer, in some cases, appear to modify the physical properties of the membrane to such a degree that the membrane itself becomes unstable and can no longer retain the drug, thus releasing it into the medium. On the basis of these observations, what should be achieved, in a drug-encapsulating system, is the protection of the liposome, by stabilization, in order to avoid the undesirable interactions between liposome/drug.

On the other hand, the use of liposomes for specific administration of a drug via blood stream is severely impaired by its rapid clearance by the cells of the reticuloendothelial system (RES), which are located mainly in the liver and in the spleen. In fact, it is well known that smaller liposomes have increased blood circulation lifetime (U.S. Pat. No. 5,225,212). However, smaller liposomes have smaller intravesicular volumes thus rendering them of little value for therapeutics. Another attempt to solve this problem has been the use of Ptx microencapsulation in structures such as liposomes and nano-spheres (Bartoni D. and Boitard R., 1990, "In vitro and in vivo antitumor activity of free and encapsulated taxol", J. Microencapsulation, vol. 7:191-197). In particular, liposome formulation has proved at least as effective as isolated Ptx. However, only those formulations containing less than 2% Ptx were physically stable (Sharma A. et al., 1995, "Antitumor efficacy of taxane liposomes on a human ovarian tumor xenograft in nude athymic mice". J. Pharm. Sci. vol. 84: 1400-4; Sharma U. S. et al. 1995 "Pharmaceutical and physical properties of paclitaxel (taxol) complexes with cyclodextrins". J. Pharm. Sci. vol. 84: 1223-30). On the other hand, nano-sphere formulations proved toxic.

An important property to be achieved in these formulations is an increase in plasma circulation time. Biodistribution studies are conducted on specifically selected organs or tissues; the contents of the lipids in the liposomes or of the drug under study in samples obtained form the homogenization of the tissues are analyzed. The aggregation of lipidic molecules with sugars, or lipids containing amino acid groups, such as GM1 monosialoganglioside, to the liposomes significantly reduces the accumulation of lipids in the liposome in the liver and in the spleen. For example, in the case of vincristine, a formulation combines a liposome internal pH of 2 and the presence of GM1 in the liposome bilayer. Intravenous administration of this formulation containing 2, 3 or 4 mg/Kg of the drug to mice inoculated with P388 tumor cells greatly increased lifetime in these mice when compared with controls. Several laboratories have also studied the possibility of increasing liposome mean circulation time by mimicking the surface of red blood cells.

The role of surface carbohydrates in the cell recognition has been widely studied (Ashwell G. and Morell A. G., 1974, "The role of surface carbohydrates in the hepatic recognition and transport of circulating glyco-proteins", Adv Enzymol 41:99-128; Hakormori S., 1981, "Glycosphingolipids in cellular interaction, differentiation, and oncogenesis". Annu Rev Biochem. vol. 50:733-764). The chemistry, metabolism and biological functions of the gagliosides and of sialic acid have also been deeply considered (Schauer, R., 1982, "Chemistry, metabolism, and biological functions of sialic acids", Adv. Carbohydrate Chem. Biochem. 40, 131-23; Ledeen R. W. et al., 1998, "Sphinglolipids as signaling modulators in the nervous system", Annals of the New Cork Academy of Science, Vol 845). It has been described that the incorporation of GM1 ganglioside into liposomes composed of phosphatidylcholine (PC) and cholesterol significantly increases their mean blood circulation time (Bedu-Addo F. K. and L. Huang, 1996, "Effect of matrix lipid chain length on liposomes containing cholesterol and GM1 ganglioside: Implications in drug delivery", Journal of Pharmaceutical Sciences, Volume 85, Issue 7, Pages 714-719).

The above stated results and comments clearly show the present need to develop formulations containing water-soluble hydrophobic substances and, at the same time, effective quantities of said active drugs, such as Paclitaxel, Docetaxel and Amphotericin B but exhibiting none of the disadvantages caused by the insolubility of the above mentioned drugs.

Other strategies for the formulation of very low water-soluble drugs have traditionally been the use of emulsions and other colloidal associations such as micelles; this being a type of structure that dissolves drugs and, besides, increases their concentration in an aqueous medium (U.S. Pat. No. 6,296, 870). However, these emulsions and, especially, micelles suspensions are not necessarily stable and do not reach specific target sites. It is known that emulsions and active agent-loaded micelles are more unstable than liposomes. In general, micelles are considered stable only when they are in balance with the surfactant monomer the micelle is formed of. Therefore, in the absence of the monomer, micelles disassemble in the water-soluble monomer and, finally, micelle totally dilutes. Likewise, in the absence of the monomer, the drops of a microemulsion coalesce in big drops, which are finally lost. Thus, when a micelle preparation dilutes, for example, due to i.v. administration, micelles dissolve and disperse in the medium, leaking their content into the blood stream in a matter of seconds. Similarly, emulsion preparations show the same instability principle.

Other mechanism of rapid removal of the micelles-encapsulated drug is carried out by the interaction with the lipoprotein.

FIGURE DESCRIPTION

FIG. 1: samples containing 100 mg monosialoganglioside GM1 (—◆—), GM2 (—■—) and GM3 (—▲—) were diluted in 1 ml distilled water at pH 5, or in 1 ml acetic-acetate buffer solution 20 mM at pH 5, by gently agitation, until completely dissolved. The solution was allowed to stand for at least 24 hs at 4 or 8° C. Then, the transparent solution was centrifuged at 50.000×g for 15 minutes and the supernatant was filtered through 0.22 micron pores. Aliquots of 0.5 ml of each 100 mg/ml monosialoganglioside solution were incubated with DMSO 50 microliters with an increasing amount of Ptx to reach the following Ptx-Gangliósíde relations: 1/25, 1/20, 1/15 and 1/10. The solutions were incubated at 4° C. for one hour and then centrifuged at 15.000×g for 15 minutes in order to remove the insoluble Ptx material that had not been encapsulated by the micelles. Finally, the samples were dialyzed in distilled water or acetic-acetate solution 20 mM at pH 5 for 24 hs in order to remove all DMSO. Ptx quantification was carried out by HPLC.

FIG. 2: samples containing 100 mg GM1 monosialoganglioside were diluted in 1 ml distilled water at pH 5, or in 1 ml acetic-acetate buffer solution 20 mM at pH 5, by gentle agitation, until completely dissolved. The solution was left to settle for at least 24 hs at 4 or 8° C. Then, the transparent solution was centrifuged at 50.000×g for 15 minutes and the supernatant was filtered through 0.22 micron pores. Aliquots of 0.5 ml of 100 mg/ml were incubated with DMSO 50 microliters with an increasing amount of Ptx to reach the following Ptx-GM1 relations: 1/100, 1/50, 1/25 and 1/11. The solutions were incubated at 4° C. for one hour and then centrifuged at 15.000×g for 15 minute in order to remove the insoluble Ptx material that had not been encapsulated by the GM1 micelles. Finally, the samples were dialyzed in distilled water or acetic-acetate solution 20 mM at pH 5 for 24 hs in order to remove all DMSO. A 400 ul aliquot of each sample was injected into a molecular filtration AKTA Explorer system using a Superdex G 200 column and a running buffer phosphate pH 7 50 mM with 50 mM NaCl 150 mM. The following molecular weights (MW) were determined:
GM1 (—■—) 365 KDa (micelles) and 1.6 KDa (monomers)
Ptx/GM1: 1/100 (—◆—)→350 KDa
Ptx/GM1: 1/50 (—✱—)→315 KDa
Ptx/GM1: 1/25 (—●—)→280 KDa
Ptx/GM1: 1/11 (—▲—)→255 KDa FIG. 3: samples containing 100 mg GM1 (—◆—), and LIGA (—■—) were diluted in 1 ml distilled water at pH 5, or in 1 ml of 20 mM acetic-acetate buffer solution at pH 5, by gentle agitation, until completely dissolved. The solution was allowed to stand for at least 24 hs at 4 or 8° C. Then, the transparent solution was centrifuged at 50.000×g for 15 minutes and the supernatant was filtered through 0.22 micron pores. Aliquots of 0.5 ml of each 100 mg/ml solution were incubated with DMSO 50 microliters with an increasing amount of Ptx to reach the following Ptx-GM1 or Ptx-LIGA relations: 1/25, 1/20, 1/15 and 1/10. The solutions were incubated at 4° C. for one hour and then centrifuged at 15.000×g for 15 minutes in order to remove the insoluble Ptx material. Finally, the samples were dialyzed in distilled water or 20 mM acetic-acetate buffer solution at pH 5 for 24 hs in order to remove all DMSO. Micelle-associated Ptx determination was carried out by HPLC.

FIG. 4: GM1 solutions were incubated with an increasing amount of Ptx in order to reach the following Ptx molar relations: 1/100, 1/50, 1/25, 1/20, 1/15, 1/10 and 1/5. Ptx micelle GM1-incorporated quantification was carried out by HPLC.

Figure 5:
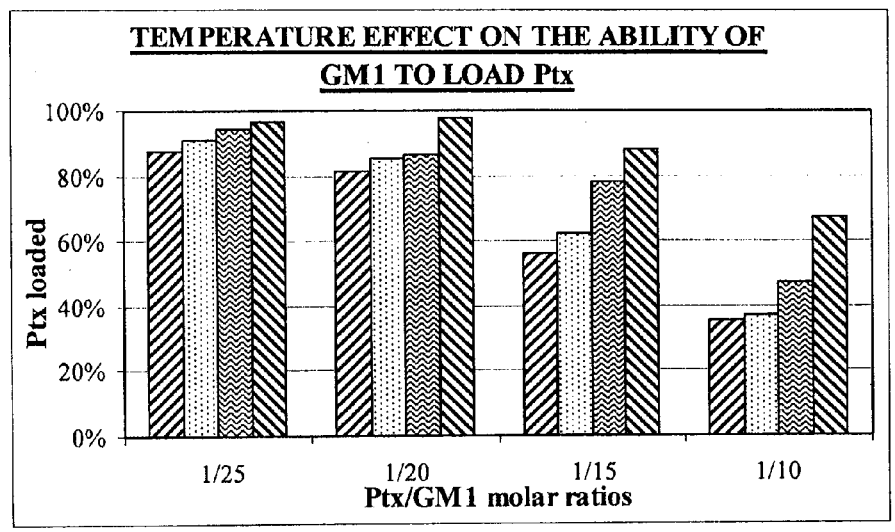

FIG. 5: Ptx was loaded into the ganglioside micelles in the following relations: 1/10, 1/15, 1/20 and 1/25. The loading was performed for 30 minutes at a temperature of A-(◨) 0° C., B-(▣) GM1 preheated at 55° C. and load of Ptx at 0° C., C-(▨) GM1 preheated at 55° C. load and load of Ptx at 25° C. and D-(■) GM1 preheated and loaded at 55° C. The amount of Ptx incorporated in soluble form into the GM1 micelle was quantified by HPLC.

Figure 6:
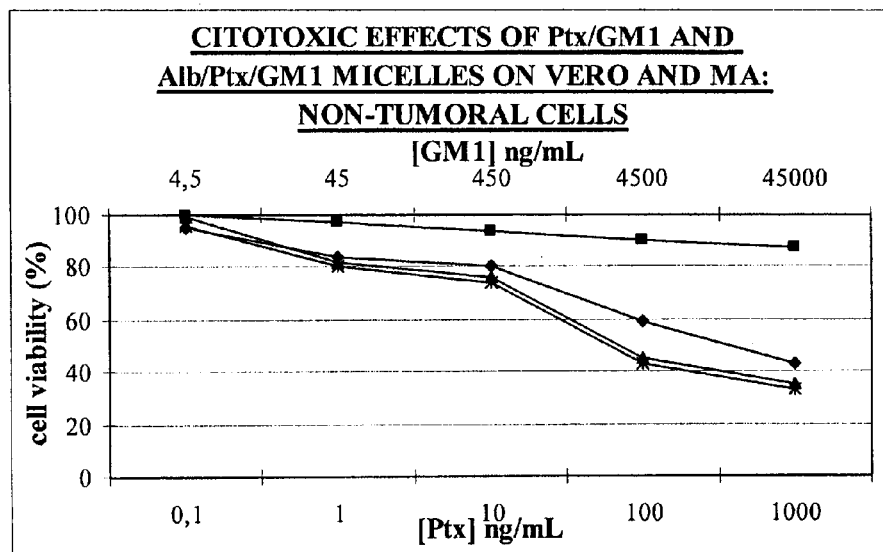

FIG. 6: VERO and MA cells of non tumoral origin were incubated with increasing concentrations of: a)-(▲) Ptx in DMSO, b)-(✱) micelles of Ptx-GM1 1/25, c)-(■) micelles of GM1 and d)-(♦) micelles of the albumine-Ptx-GM1 complex. Cellular viability was evaluated using MTT assay marker after 24 hs incubation.

Figure 7:
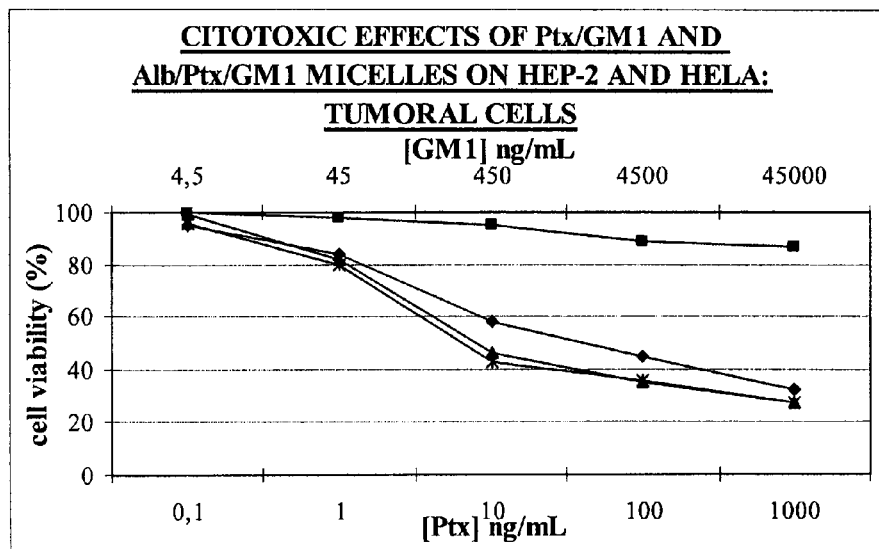

FIG. 7: HEP-2 and HELA cells of tumor origin were incubated with increasing concentrations of: a)-(▲) Ptx in DMSO, b)-(✱) Ptx-GM1 micelles 1/25, c)-(■) GM1 micelles and d)-(♦) micelles of the GM1-Ptx-albumine complex. Cellular viability was evaluated using MTT assay after 24 hs incubation.

Figure 8:
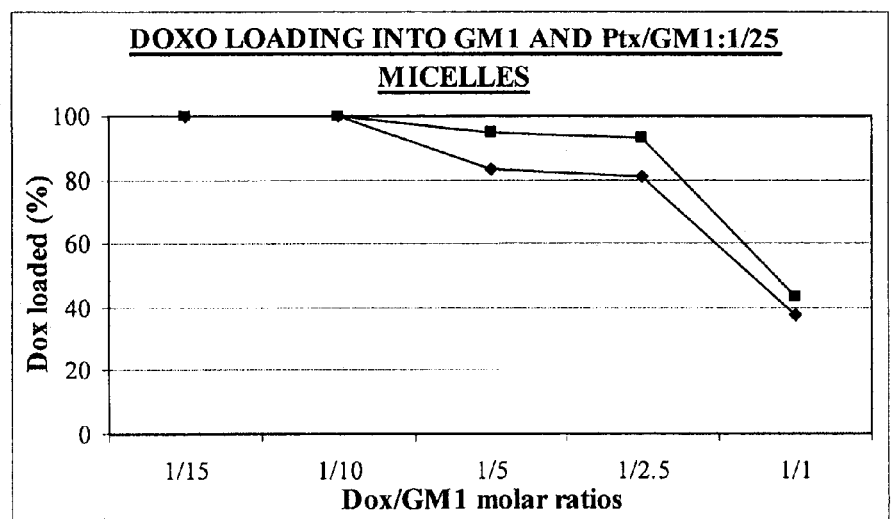

FIG. 8: samples of GM1 (♦) and Ptx-GM1 complexes: 1/25 (■) were incubated with increasing concentrations of Dox, in order to reach molar relations of the Dox-GM1 complex of 1/10, 1/5, 1/2.5 and 1/1. Quantification of Dox incorporated into the micelles was performed by spectrophotometry at 492 nm.

FIG. 9: GM1 micelles with 5 mg/ml of GM1 were incubated with increasing amounts of purified human serum albumin in order to reach the following concentrations: 0.83, 1.67, 5, 15 and 30 mg/ml (final concentration); these represent GM1-Alb relations w/w: 6/1 (■), 3/1 (✱), 1/1 (▼), 1/3 (♦) and 1/6 (▲), respectively. Incubations were carried out at 37° C., for 3 hours. Figure A corresponds to the complete chromatography run, while B represents the insert pointed out in A, and which corresponds to the peaks at higher MW.

FIG. 10: Ptx-GM1 micelles with 5 mg/ml of GM1 and a Ptx-GM1 molar relation of 1/25 were incubated with increasing amounts of purified human serum albumin in order to reach the following concentrations: 0.83, 1.67, 5, 15 and 30 mg/ml (final concentration); these represent GM1-Alb relations w/w: 6/1 (■), 3/1 (✱), 1/1 (▼), 1/3 (♦) and 1/6 (▲), respectively. Incubations were carried out at 37° C., for 3 hours. Figure A corresponds to the complete chromatography run, while B represents the insert pointed out in A, and which corresponds to the peaks at higher MW.

FIG. 11: Ptx-GM1 micelles with a Ptx-GM1 molar relation of 1/25 were incubated with a fixed amount of purified human serum albumin in order to reach GM1-Alb relation w/w: 1/1. Incubations were carried out at 4° C. for 1 h (■), 4 hs (✱) and 24 hs (▼). Figure A corresponds to the complete chromatography run, while B represents the insert pointed out in A, and which corresponds to the peaks at higher MW.

FIG. 12: Ptx-GM1 micelles with a Ptx-GM1 molar relation of: 1/25 were incubated with a fixed amount of purified human serum albumin in order to reach GM1-Alb relation W/W: 1/1. Incubations were carried out at 37° C. for 1 h (■), 4 hs (✱) and 24 hs (▼). Figure A corresponds to the complete chromatography run, while B represents the insert pointed out in A, and which corresponds to the peaks at higher MW.

FIG. 13: Ptx-GM1 micelles with Ptx-GM1 molar relation of 1/25 were incubated with a fixed amount of purified human serum albumin in order to reach GM1-Alb relation W/W: 1/1. Incubations were carried out at 55° C. for 1 h (■) and 4 hs (✱). A sample of albumin incubated for 4 hs at 55° C. (▼) is also included in the figure as control of the protein stability at that temperature.

FIG. 14: GM1 solutions were incubated with AmB in order to obtain a GM1 to AmB final molar relation of 1/5 (✱), 1/1 (▼), 5/1 (♦) and 25/1 (▲). An absorption spectrum of each sample from 300 to 500 nm was drawn. A sample of AmB in ethanol (■) as control of the monomeric state adopted by AmB is annexed to the figure. Samples 1/5 and 1/1 adopt an aggregate form that show an absorption maximum at 345 nm; while samples 5/1 and 25/1 adopt a monomeric form with maximum absorption peaks at 365, 385 and 410 nm.

FIG. 15: AmB-GM1 micelles with molar relations between 5/1 (♦) 2.5/1 (♦) 1/1 (+) and 1/2.5 (✱) were prepared using a fixed concentration of AmB of 16 ug/ml. A GM1 (■) micelle control and another AmB (▲) control were prepared to study the effect of each one in a separate form; also, a positive control (■) and a negative one (♦) were prepared to observe the micro organism growth. The different preparations of GM1-AmB and their respective controls were incubated with a *candida Albicans* solution at a concentration of 1×10⁵ cells/ml on a 96 well plate for 24 hs at 37° C. Serial dilutions were made on the plate until a final concentration of AmB of 0.0625 ug/ml was reached. After incubation, the turbidity of the solution, which shows the micro organism growth, was evaluated by spectrophotometry at 610 nm.

BRIEF DESCRIPTION OF THE INVENTION

This invention is about water soluble pharmaceutical compositions that have, at least, one therapeutically active substance and, at least, one compound selected from among the sialoglycosphingolipids, the glycosphingolipids or a mixture of sialoglycosphingolipids and glycosphingolipids and in which, at least, one of the therapeutically active substances is a drug with hydrophobic characteristics. Preferably, the drug with hydrophobic characteristics is chosen from among the antitumor drugs and the antimicotic ones.

In particular, a composition in agreement with the invention shall be adequate for i.v. administration to a patient. More particularly, the composition of the invention is a sterile and translucid injection.

Preferably, the pharmaceutical composition of the invention includes, at least, one glycosphingolipid which is, preferably, selected from among the gangliosides. In particular embodiments, the gangliosides are selected from among the monosialogangliosides, the disialogangliosides, the trisialogangliosides or a mixture of them. More particularly, the monosialogangliosides are selected from among the GM1, GM2 or a mixture of them, the disialogangliosides are selected from among the GD1a, GD1b or a mixture of them and the trisialoganglioside is GT1. The invention also makes provisions for the pharmaceutical composition to have a mixture of monosialogangliosides and trisialogangliosides or a mixture of disialogangliosides and trisialogangliosides, or a mixture of monosialogangliosides, disialogangliosides and trisialogangliosides.

DETAILED DESCRIPTION OF THE INVENTION

In order to use adequately a micelle structure as a load and delivery system to release drugs in the blood stream, it is necessary to improve the behaviour of the micelles mentioned in "State of the Art" according to the following key aspects:

1—Avoid the problems related to the micelles dissolution caused by the dilution phenomenon,
2—Obtain a structure with a surface or with physicochemical and/or electric properties that mimic the red blood cells in order to avoid their interaction and,
3—Enable the micelles to be coated by polymers or proteins that can: i) stabilize the micelle—drug complexes and/or ii) serve as agents to deliver the micelles to the target.
4—Obtain a structure as small as possible in order to avoid the rapid release into the blood stream by the RES.

5—In opposition, it should have a M/W higher than 40 kDa, in order to avoid rapid elimination by the renal system.

The authors of the present invention have developed a novel strategy that considerably improves the problems of the above mentioned in "State of the Art" and, in particular, have developed a new formulation on the basis of stable nano-micelles which permit to load high concentrations of hydrophobic drugs.

Thus, the present invention proposes the use of a new type of micelles based on the use of amphipatic molecules such as gangliosides. These molecules are characterized by showing, in opposition to all the other polymeric micelles, a very low critical micelle concentration (cmc). Gangliosides and, especially, GM1 and GM2 monosialogangliosides show a cmc of about $10^{-8}$ M, which substantially increases micelle structure stability. In particular, the use of gangliosides over their cmc is proposed. This, permits to obtain high content sialic acid structures and, thus, obtain electronegativity similar to that in the red blood cells.

The importance of the presence of sialic acid in the ganglioside molecules and in the glycoproteins such as glycophorin in the properties of the cell membrane surface has already been mentioned. Besides, sialic acid plays a role in the GR lifetime, in the trombocites and in the lymphocytes in the circulation. Enzymatic removal of sialic acid, which exposes the galactose terminal, results in a rapid removal of the circulating GR and in their capture by the Kupffer cell of the liver.

In a particular embodiment, the authors describe that the MW of the gangliosides micelles with paclitaxel ranges from 150 and 350 kDa.

The authors of the present invention have been able to show the high stability of the ganglioside micelles, in particular those composed of GM1 by means of the dialysis. Results show that about 25% of the total GM1 micelles is lost 72 hs after dialysis; these results are in agreement with those published by Formisano et al. ("Critical micelle concentrations of gangliosides"; 1979, Biochemistry 18:1119-1124). However, if micelles are loaded with a hydrophobic drug, such as Ptx or Dtx, forming the GM1-Ptx or GM1-Dtx complex, the amount of GM1 and drug lost by dialysis is now lower than 5% and 10%, respectively; this shows that the hydrophobic molecule may regulate the micelle dissociation mechanisms itself, thus favouring stabilization of the micelle form. Likewise, ganglioside micelles, especially those composed of GM1, may be loaded with other oncological drugs, such as Doxo, to form the GM1-Doxo complex.

In a particular embodiment, the micelle system composed of gaglioside, especially GM1 glangliosides, permits the simultaneous incorporation of two oncology drugs on the same micelle surface: the most hydrophobic ones such as Ptx or Dtx, into the micelle core and the most hydrophilic one such as Doxo in another micelle domain; in this way, a stable and water soluble GM1-Ptx-Doxo ternary complex is obtained.

Under the conditions proposed by this invention, GM1 nano-micelles and also the GM1-Ptx or GM1-Ptx-Doxo ones can interact in a spontaneous and non-covalent way and by means of a hydrophobic-like interaction with the albumin molecule in order to compose a new highly stabilized complex or structure. Said complex could trigger transcytosis through the endothelial cells towards the interstitial medium, by binding the albumin to the receptor (SPARC); this being the area where the tumour tissue is located, as has been demonstrated by the albumin-Ptx complex (called ABI007).

On the other hand, and in particular embodiments, the GM1-Ptx complex can be delivered to humans by previous injection into transfusion bags containing human albumin, whole human serum or complete human plasma; this is where the GM1-Ptx complex specifically binds to the albumin to render the ternary or quaternary complex biologically active, GM1-Ptx-Alb or GM1-Ptx-Doxo-Alb.

One advantage of the compositions in the present invention is that the solubility retention in an aqueous medium of a hydrophobic bioactive agent is increased by the high stability in these ganglioside micelles, due to their low cmc (which is about $10^{-8}$M); due to this, the bioactive agent circulation time in this structure is increased. On the other hand, the therapeutic activity of this composition is significantly improved because it also produces an important decrease in the undesirable side effects.

Therefore, one of the objectives of this invention is to introduce a formulation containing a sialoglycosphingolipid-micelle composed carrier, a mixture of sialoglycosphingolipids or glycosphingolipids modified over their cmc, especially by ganglioside micelles, more in particular by monosialogangliosides and, preferably, by GM1, GM2 micelles or a mixture of them that permit the non-covalent incorporation of hydrophobic drugs. In particular, the invention encompasses formulations that present a ganglioside-nano-micelle composed carrier where the ganglioside is the GM1, especially, which permits the incorporation in a non-covalent way, of hydrophobic drugs such as Ptx, Dtx Ο Amphotericin B, in such a way that it permits the appearance of a highly hydro soluble complex, which can also be selectively coated, in a non-covalent way, by means of a hydrophobic interaction with a plasma protein such as albumin.

Therefore, one objective of this invention is to create a water soluble pharmaceutical composition containing, at least, one therapeutically active substance and, at least, one or more compounds selected from the sialoglycosphingolipids, the glycosphingolipids or a mixture of sialoglycosphingolipids and glycosphingolipides, and in which, at least, one of the therapeutically active substances is a drug with hydrophobic characteristics. In particular embodiments, said therapeutically active substances are chosen from among the antitumor drugs and the antimicotic ones; in other embodiments, they are chosen from among antibiotic and steroid hormones.

As used in the present invention, the terms "therapeutically active substances" "drugs" "active principles" "active agents" and "bioactive substances" should be understood as equivalent.

In accordance with a preferred embodiment, the pharmaceutical composition of this invention is adapted for i. v. administration. Even more preferably, it is a stable and translucid i. v. composition. In particular, the water soluble pharmaceutical composition of this invention can be lyophilized or found in a lyophilized form. In this case the composition can be reconstituted with a solvent such as distilled water, saline solution (NaCl 0.9%), saline phosphate buffer solution (PBS), distilled water containing 5% dextrose and saline solution with 5% dextrose. It is also a particular objective of this invention to produce a water soluble and sterile lyophilized pharmaceutical composition that can be resuspended so that antitumor drugs such as Dtx Ο Ptx can reach a final concentration ranging from 0.1 to 10 mg/ml, preferably, from 0.1 to 6 mg/ml, and even more preferably, from 1 to 6 mg/ml.

Preferably, the water soluble pharmaceutical composition of this invention shall have, at least, one therapeutically active substance and one or more glycosphingolipids; these last ones being preferably selected from among the gangliosides. Even more preferably, from among the gangliosides, the monosialogangliosides, the disialogangliosides, the trisialogangliosides or a mixture of them is preferred. In an even more preferred embodiment, the monosialogangliósidos are selected from among the GM1, GM2 or mixture of them; the disialogangliosides are selected from the GD1a, GD1b or a mixture of them and the trisialoganglioside es GT1. Likewise, the preferred mixtures of gangliosides are selected from a mixture of monosialogangliosides and disialogangliosides, a mixture of monosialogangliosides and trisialogangliosides, a mixture of disialogangliosides and trisialogangliosides and a mixture of monosialogangliosides, disialogangliosides and trisialogangliosides Preferably, in the water soluble pharmaceutical composition of this invention, the drug or drugs with hydrophobic characteristics are bound to the gangliosides in a non covalent way and the gangliosides form nanomicelles. Even more preferably, the nanomicelles pH ranges from 3 to 7. In an even more preferred embodiment the naonomicelle pH ranges from 4 to 6.

Particularly, water soluble pharmaceutical compositions of this invention, nanomicelles are, on average, smaller than 200 nm; even more particularly, smaller than 100 nm, preferably, between 10 nm and 80 nm and, even more preferably, between 10 nm and 50 nm.

Gangliosides are amphipatic molecules having a lipophilic domain formed by sphingosine and a fatty acid, such as stearic acid, and a hydrophilic domain formed by carbohydrates that include, at least, between one and four monosaccharides, and between one and three sialic acid molecules, which give rise to the different known gangliosides. These complex glycolipids are known to be water soluble acids and can be poorly dialyzed. Since gangliosides are mainly associated to nerve tissue membranes, it has been suggested that they could play a role in the transfer of information through these membranes (Ledeen R. W. y col., 1998, "Sphinglolipids as signaling modulators in the nervous system". Annals of the New Cork Academy of Science Vol 845). In particular, the GM1 monosialoganglioside has been associated with processes of neuronal differentiation in mouse cerebellum (Willinger M. and Schachner M., 1980, "GM1 ganglioside as a marker for neuronal differentiation in mouse cerebellum", Dev Biol. 74(1):101-117) and also with receptor for the cholera toxin (Wu, G. and Leeden, 1988, "The ganglioside-GM1 is the specific receptor for the cholera toxin", Anal R. Biochem., vol. 173, p. 368-375).

The gangliosides to be used in the present invention can be obtained from animals having these lipids. In particular, they can be obtained from nerve tissue from animals selected from mammals and non-mammals such as felines, bovines, pigs, horses and fish.

The ganglioside micelles in the present invention are versatile, and can solubilize and associate not only with highly water soluble molecules or macromolecules but also with the insoluble ones. A micelle is a colloidal association having regions with a strong anisotropy and a water soluble decreasing gradient that goes from the outside to the inside of it. This is one of the properties that render the micelles capable of solubilizing a wide range of other solutes.

Micelles can solubilize insoluble organic matter due to their capacity to incorporate said matter into its highly hydrophobic region. On the outmost part of the hydrocarbonated chain, the three or four carbon atoms are all trans and, therefore, it is a less fluid domain. Thus, this region is weakly hydrophobic, so it could be partially hydrated. In this manner, this represents a transition area between the purely hydrophobic area and the purely hydrophilic one. Molecules entering this area must be slightly compatible with both the hydrophobic area of the lipidic chain and the solvated region of the polar head and, therefore, they must behave as amphipatic molecules. In the case of active principles with hydrophobic characteristics, these tend to set directly in the deep region of the micelle through the interaction with the hydrophobic chains of the fatty acids.

With respect to the micelle polar head, there is a wide range of compositions; this implies the possibility of having a range of characteristics of different surfaces in each type of micelles that can be used to associate a range of active agents. In the case of this type of ionic micelles, the region of the polar head can bind a big amount of counter ions; therefore, it is similar to an electrolyte-concentrated solution. Even more so, the diffuse ionic bilayer, found in the loaded micelles, extends over the, so called, Stern layer.

Micelles can dissolve active agents and constitute an excellent system to capture and incorporate insoluble or partially insoluble molecules. It has been proposed that this molecule partition could be limited to relatively small molecules that can accommodate to the highly anisotropic structure of the fatty acid chains either because they occupy the intermediate region or because they can accommodate within the fatty acid chains. Thus, micelles can act as an active agent for the transport of completely or partially water insoluble drugs going straight to the hydrocarbonated chains of the stearic acid.

The present invention describes a varied composition of lipidic micelles having bioactive agents, the methods for their obtention and their use. In an aspect of the present invention, a series of micelle formulations that can incorporate, on the one hand, the bioactive agents and, on the other hand, a buffer solution with a pH between 3 and 7 is described.

In a particular embodiment of this invention, the water soluble pharmaceutical composition includes 1 part of disialogangliosides for each part of 5 and 15 parts of monosialogangliosides. In another, it includes 1 part of trisialogangliosides for each part of 5 and 15 parts of monosialogangliosides; in another, it includes 1 part of trisialogangliosides and 10 parts of disialogangliosides.

In another particular embodiment, the water soluble pharmaceutical composition in this invention includes one or more glycosphingolipides chosen from among the gangliosides containing covalent folic acid coupled to the glycosidic domain or gangliosides containing covalent folic acid coupled to sialic acid. In particular, gangliosides containing coupled covalent folic acid stand for 0.5% and 15% of the total of the gangliosides in the composition.

In preferred embodiments of this invention, the water soluble pharmaceutical composition includes Ptx or Docetaxel (Dtx). Preferably, it includes Ptx or Dtx in a molar ratio drug:ganglioside ranging from 1:10 to 1:100. More preferably, ranging from 0.1 mg/ml to 6 mg/ml of Ptx o Dtx and ranging from 4 mg/ml to 300 mg/ml gangliosides. In another special embodiment, the water soluble pharmaceutical composition of the invention includes Doxo in a molar ratio Doxo:ganglioside of 1:1 and 1:50. In another specially preferred embodiment, the water soluble pharmaceutical composition of the invention includes Doxo and, at least, a drug selected from Ptx and Dtx in a molar ratio for each of the drugs:ganglioside of 1:10 and 1:100.

In another preferred embodiment of this invention, the water soluble pharmaceutical composition includes amphotericine B, preferably, in a molar ratio amphotericine B:ganglioside ranging from 2:1 to 1:5. Even more preferably, in a molar ratio amphotericine B:ganglioside of 01:1. In another preferred embodiment, it includes a ratio ranging from 0.1 mg/ml to 10 mg/ml amphotericine B and ranging from 0.18 mg/ml to 10 mg/ml gangliosides.

In a specially preferred embodiment of this invention, the water soluble pharmaceutical composition includes ganglioside nanomicelles non-covalently coated with human seric albumin, recombinant human seric albumin or with bovine albumin, more preferably, with human seric albumin containing fatty acids. Even more particularly, they are coated with human seric albumin, with or without fatty acids in a GM1-albumin ratio 2:1 W/W.

In another special embodiment, this invention includes a water soluble pharmaceutical composition in which the ganglioside nanomicelles are coated with albumin containing covalently coupled folic acid; even more particularly, the amount of folic acid covalently coupled to the albumin ranges from 1 to 20% of the total albumin.

As an example, for administration to a patient the water soluble pharmaceutical composition of this invention could be injected into a plastic bag (similar to the ones used for transfusion) containing human albumin in order to permit the union of the GM1-Ptx, GM1-Dtx, GM1-Ptx-Doxo, GM1-AmB nonomicelles to the albumin.

It is noteworthy that the loading procedure of the micelles as described in the present invention shows an important difference regarding the general methods used for loading liposomes with bioactive agents by using a transmembrane potential across the lipidic bilayer of the liposome according to what is described in U.S. Pat. No. 5,171,578 and U.S. Pat. No. 5,077,056, for example.

The formulations in the present invention can be prepared by means of a passive load method. For example, the bioactive agents can be encapsulated in ganglioside nonomicelles at high concentrations using a simple method such as incubation at low or high temperatures during which incorporation takes place spontaneously. On the other hand, GM1 micelle coating with human serum albumin occurs in a non-covalent spontaneous manner and by means of a hydrophobic-like interaction; this coating finally generates either a ternary complex made up of GM1-drug-albumin or, when the albumin has incorporated folic acid in a covalent way, a quaternary complex: GM1-drug-albumin-folic acid.

The procedure could be summarized as follows: the GM1 monosialoganglioside is diluted in distilled water by shaking it slowly and then it is allowed to stand at 4 and 8° C. for, at least, 24 hs. This incubation time could permit the ganglioside micelles to become a stabilized structure smaller than 200 nm in size. Then, ganglioside micelles are incubated in a tenth of their volume (1/10 vol/vol) with solvents such as ethanol or dimetilsulfoxide containing the completely soluble hydrophobic tumour drug. The samples are incubated at a temperature of 4 and 8° C. for, at least, 4 hs. Then the organic solvent is removed from the ganglioside micelles by dialysis. This dialysis is carried out with an i.v. pharmaceutical-grade solution with the adequate pH. The drug-incorporated micelle formulation, essentially free of solvents and with the desired pH, is centrifuged at between 15.000 and 30.000×g for 15 minutes in order to remove the insoluble and undesirable hydrophobic compounds that were not incorporated into the micelles.

The nano-micelles transparent aqueous formulation containing the entrapped or encapsulated antitumoural or antimicotic drugs is then incubated with purified human albumin, purified human albumin containing covalently coupled folic acid, human total plasma or total human serum in order to ensure interaction albumin/GM1 micelles. This incubation can be carried out at 37° C. for 8 hs, or at 55° C. for 30 minutes. The formulations composed of GM1 and Ptx or GM1-Ptx-Albumin complexes are finally lyophilized.

Thus, the present invention also refers to a procedure to obtain micelles containing, at least, one hydrophobic bioactive encapsulated agent; this procedure encompasses the following stages:

(a) Solubilize the gangliosides in distilled water or in a in a saline solution with a pH ranging from 3 to 7, always over the cmc, allowing the solution to stand at 4° C. for, at least, 24 hs;

(b) Add about 10% of a solution of dimethylsulphoxide or ethanol with the chosen bioactive agent to the ganglioside micelles solution obtained according to the previous stage;

(c) Incubate said mixture at low temperatures, between 4 and 8° C., or at high temperature between 45 and 60° C., for a sufficient time, preferably between 1 and 4 hs in order to ensure the correct incorporation of the bioactive agent to the micelles and then;

(d) Dialize the micelle solution containing the bioactive principle with a distilled water solution or a pharmaceutically acceptable solution with a pH between 3 and 7, for 24 hours at a temperature between 4 and 8° C., in order to remove the organic solvent completely;

(e) Incubate the micelles composed of GM1-drug complex with human serum albumin for one hour at a temperature between 45 and 60° C., or for 8 hours at a temperature of 37° C. in order to allow the formation of the GM1-drugs-albumin ternary complex;

(f) Sterilize the aqueous and transparent solution obtained from the previous stage, which contains the hydrophobic bioactive agent incorporated into the GM1 micelle by filtration by 0.1 or 0.2 microns;

(g) Lyophilize the sterilized micelles and finally, (h) Resuspend the lyophilized micelles in a pharmaceutically acceptable solution for i.v. administration for the treatment of the pathology.

The amount of the different bioactive agents incorporated (Ptx, Dtx, Doxo, AmB, etc.) into the ganglioside nanomicelles can be determined using spectroscopic techniques or appropriate chromatographic techniques such as high-pressure liquid chromatography (HPLC).

The nanomicele gangliosides can be loaded using the suitable solvent. In particular, they can be loaded with the antitumor agent, e.g. Dtx or Ptx, previously solubilized in organic solvents such as ethanol or dimethylsulphoxide. In particular embodiments, the amount of ethanol or dimethylsulphoxide used for the incorporation of docetaxel and paclitaxel in the nanomicele gangliosides ranges from 1 to 15% of the total volume. Likewise, they can also be loaded in a temperature range from 4 to 6° C.

The solvents used to load the nanomicelles and/or the free therapeutically active substance can be removed by a procedure adapted to this purpose. For example, they can be removed by dialysis or by molecular filtration using Sephadex G25.

As previously mentioned, one or more drugs can be loaded into these stable monosialoganglioside nanomicells using the above mentioned passive incorporation method. In summary, using the nanomicelle composition of the invention, it is possible to obtain an aqueous transparent solution for most hydrophobic drugs, which tend to partition and stabilize in the hydrophobic ganglioside micelle region composed of ceramide.

Other drugs, similar to Ptx, Dtx, Dox, AmB and progesterone and that can be incorporated into the compositions of the invention, are those that are defined by a partition coefficient oil/water as a measure in an oil/water standard mixture such as octanol/water larger than 1, preferably larger than 5.

The representative drugs in this category include prostaglandins, isosorbide dinitrate, testosterone, nitroglycerin, estradiol, vitamin E, cortisone, dexamethasone and esters and its esters and betamethasone valerate.

Ganglioside micelles show different capabilities to incorporate drugs depending on their structure and form. In this sense, the results obtained by the authors of this invention, clearly show that as the oligosaccharide hydrophilic chain size decreases from GM1 to GM2 and then to GM3, there is a change in the structure of these lipids. This means that GM1 and GM2 retain a micelle structure, while GM3 no longer has a micelle structure: it has a vesicle one. These structure changes result in a decrease in the drug incorporation; these capabilities being the highest for GM1, lower for GM2 and substantially lower for the least effective structure formed by GM3. (See FIG. 1)

A study of electron microscopy shows that GM1 micelles of this invention are not spherical but ellipsoid. The results reveal that the mixture hydrophobic drug/micelle produces a change in the micelle size. This change, contrary to expectations, demonstrates that the incorporation of paclitaxel into the GM1 micelle to form the GM1-Ptx complex produces a decrease in its molecular weight. (See FIG. 2)

Without referring to any explanation in particular, this result could be explained by, at least, two hypotheses: that there is a decrease in the number of GM1 monomers in the micelles, produced by the drugs, or by a change in the micelle form produced by the drug that could make the micelle transform from an ellipsoid into a sphere generating a smaller hydrodynamic radius which finally results in a lower M/W.

On the other hand, it is widely known that a factor affecting the geometry of the micelles is the aggregation number, which in turn, is monomer-structure dependent. In this study, in particular, when the GM1 micelles are formed by GM1 monomers, in which the stearic acid is removed and replaced by the fluor-acetyl group, a new compound called LIGA is produced. This new type of GM1 micelle undergoes a change in the number of aggregation, from 300 to 100-120 GM1 units (LIGA). This produces a decrease in the micelle size which becomes a marked decrease in the drug incorporation. (See FIG. 3)

EXAMPLES

Example 1

Paclitaxel Loading into GM1 Gangliosides

GM1 monosialoganglioside samples containing 30, 100, 300 and 600 mg were dissolved in 2 ml of distilled water at pH 5 or 2 ml of the acetic-acetate buffer solution at 20 mM pH 5 by shaking in order to obtain a complete dissolution. The solution was allowed to stand for at least 24 hours at 4 or 8° C. The transparent solution was then centrifuged at 50.000×g for 15 minutes and the supernatant was filtered through 0.22 μm pores.

An aliquot of 0.5 ml of each concentration (15 mg/ml, 50 mg/ml, 150 mg/ml and 300 mg/ml, respectively) were incubated with DMSO 50 μl containing an increasing number of paclitaxel (Ptx) in order to reach the following Ptx-GM1 molar ratios: 1/100, 1/50, 1/25, 1/20, 1/15, 1/10 and 1/5. The solutions were incubated at 4° C. for an hour and then centrifuged at 15,000×g for 15 minutes in order to remove the Ptx insoluble material that had not been encapsulated into the GM1 micelles. Finally, in order to remove all DMSO, the samples were dialyzed with distilled water or 20 mM acetic-acetate solution at pH 5 for 24 hours.

The Ptx quantification incorporated into the GM1 micelles was carried out by using HPLC. FIG. 4 shows that the Ptx percentage that remains soluble coupled to GM1 is virtually constant from the ratio 1/100 to 1/25; in this ratio, the amount of Ptx incorporated represents 95% of the total Ptx added to the medium. At increasing ratios of 1/25 to 1/5, a decrease in the amount of Ptx soluble coupled to GM1, ranging from 90%, 60%, 30% to 10%, respectively, is observed.

Example 2

Temperature Effect on the Ptx Load in GM1 Micelles

Ptx is loaded into the gangliosides micelles in 1/10, 1/15, 1/20, 1/25 molar ratios as shown in example 1, but each load is performed for 30 minutes at a temperature of:
 1) A—0° C. (Control)
 2) B—GM1 preheated at 55° C. and Ptx load at 0° c.,
 3) C—GM1 preheated at 55° C. and Ptx load at 25° C.,
 4) D—GM1 preheated and loaded at 55° C.

After incubation, samples were centrifuged at 15.000×g for 15 minutes and dialyzed with distilled water for 24 hours at 4° C. Finally, the amount of Ptx incorporated into GM1 micelle in a soluble form was quantified by HPLC. FIG. 5 shows that, in the 1/25 ratio, the change in temperature at which the Ptx is loaded does not produce a significant increase in the incorporation; the load in all conditions being higher than 90%. However, in higher ratios, an increase of 20%, 50% and 80% respectively, in the Ptx load when it is carried out at 55° C. compared to load at 0° C. is observed.

Example 3

In vitro Comparative Study of Ptx-GM1 Versus Ptx on Tumor and Non-Tumor Cell Culture Different cell types, tumoral such as HEP-2 and Hela, and non-tumoral as VERO and MA were incubated in MEM medium containing 2% fetal bovine serum (Natocor-Villa Carlos Paz—Córdoba—Argentina) in a $CO_2$ incubator with 5% $CO_2$, to confluence. Different concentrations of the compositions mentioned below were added to the cell culture:
 a)—Ptx in DMSO as positive control
 b)—Ptx-GM1 micelles 1/25 molar ratio
 c)—GM1 micelles in equal concentrations as in b), to control the effect of the GM1 itself, and
 d)—micelles of the albumin-Ptx-GM1 complex Cell viability was evaluated by MTT assay after 24 hours of incubation.

FIGS. 6 and 7 show that the isolated GM1 has no effect on any cell type while the Ptx in DMSO and Ptx-GM1 formulation produce complete death with 24 hours up to a concentration of 10 ng/ml in tumoral cells and up 100 ng/ml in the non-tumoral ones. When the formulation has the albumin-Ptx-GM1 ternary complex, a concentration of 20 ng/ml in the tumoral cells and of 200 ng/ml in the non-tumoral is necessary to reach the same effect.

Example 4

Doxorubicin Incorporation in GM1 or Ptx-GM1 Micelles

Purified GM1 monosialoganglioside 10, 30, 150, 300 and 600 mg were solubilized by stirring in 2 ml of distilled water (pH 5) or in an acetic-acetate 20 mM buffer solution at pH 5, until its complete dissolution. The solution was allowed to stand for 24 hours, at least, at a temperature of between 4 and 8° C. The Solution was centrifuged at 50.000×g for 15 minutes and the supernatant was filtered through 0.22 um pores. Two Doxorubicin loading assays were carried out with this preparation:

(a) doxorubicin with GM1 and (b) doxorubicin in the Ptx-GM1 complex.

Point a), an aliquot of 0.5 ml of each preparation containing 15 mg/ml, 75 mg/ml, 150 mg/ml and 300 mg/ml was incubated with 50 ul of Doxorubicin solution in order to reach a molar ratio of the Dox-GM1 complex of 1/15; 1/10; 1/5; 1/2.5 and 1/1. Solutions were incubated again at 4° C. for an hour and then they centrifuged at 15.000×g for 15 minutes to remove possible insoluble aggregates. Finally, the samples were dialyzed for 24 hs at 4° C. in order to remove possible free Doxorubicin.

Point b), GM1 micelles were previously loaded with Ptx in order to reach the Ptx-GM1 molar ratio 1/25 and then the essay described in point a) was carried out.

Quantification of doxorubicin incorporated into the GM1 micelle was performed by spectrophotometry at 490 nm.

FIG. 8 shows that Doxo percentage coupled to GM1 and Ptx-GM1 is virtually constant from 1/15 to 1/10 molar ratio. At increasing ratios from 1/5 to 1/1, a decrease in the amount of Doxo ranging from 5%, 8% to 55%, respectively, is observed for GM1 micelles and a decrease of 15%, 20% and 62% in the amount of Doxo is observed for Ptx-GM1 micelles.

Example 5

Albumin Incorporation into GM1 and Ptx-GM1 Micelles

GM1 and Ptx-GM1 micelles containing 5 mg/ml of GM1 and a molar relation Ptx-GM1 1/25, as described in the previous examples, were prepared. These micelles were incubated with increasing amounts of purified human serum albumin (Laboratorio de Hemoderivados dependiente de la Universidad Nacional de Córdoba) in order to reach the following concentrations: 0.83, 1.67, 5, 15 and 30 mg/ml final concentration. The incubations were performed at 37° C. for 3 hours.

As shown in FIGS. 9 and 10, when GM1 and Ptx-GM1 micelles are incubated with albumin at 37° C., it is observed that, as a result of the association, there appear three populations with different M/W, composed of GM1, Alb and Ptx. One of them has a M/W of about 600-700 kDa that progressively increases with the albumin concentration, another has M/W of 500-550 kDa and the last one a M/W of 180-190 kDa.

On the other hand, incubations of Ptx-GM1 micelles 1/25 with GM1 5 mg/ml and albumin 5 mg/ml were also performed at three temperatures: 4, 37 and 55° C. for periods ranging from 1 to 24 hours.

As shown in FIGS. 11, 12 and 13, corresponding to incubations with albumin at 4, 37 and 55° C. respectively, there is an interaction of the Ptx-GM1 complex with albumin added to the medium in the three studied temperatures. This interaction reaches its maximum peak more rapidly at higher temperatures.

Example 6

Amphotericin B (AmB) Incorporation into GM1 Micelles

Spectral Analysis of the Complex Formation

A volume of 0.9 ml of $H_2O$ containing different concentrations of GM1 was incubated with 0.1 ml of AmB in DMSO (40 mg/ml), in order to obtain a final molar ratio GM1/AmB of: 1/5, 1/1, 5/1 and 25/1. The samples were incubated for 10 minutes at room temperature and then dialyzed for 24 hs at 4° C. Finally, the resulting solution was centrifuged at 15,000×g for 15 minutes in order to remove possible insoluble aggregates. An aliquot of the solution was taken and diluted 200 times in ethanol, in order to determine the amount of AmB incorporated into GM1 micelles by measuring the absorbance at 410 nm and comparing it with a control curve of AmB processed under the same conditions.

In addition, the presence of the monomeric state or AmB aggregate states were evaluated by spectral analysis from 300 to 500 nm; to this end, the dilution was carried out in $H_2O$ in order not to modify the aggregation state. (See FIG. 14). When AmB concentration increases in each evaluated ration, there is a change in the intensity of the peaks. This fact can be explained by the existence of two main AmB spectral states: a monomeric form that presents maximum absorptions at 365, 385 and 410 nm and an AmB aggregated form at 345 nm.

Example 7

Growth Inhibition of *candida Albicans* by the Activity of Amphotericin B-Loaded Micelles GM1-AmB micelles with molar ration between 1:5, 1:2.5, 1:1 and 2.5:1 were prepared, using a fixed concentration of 16 ug/ml of AmB. On the other hand, controls of GM1 micelles and AmB were prepared. A volume of 100 ul of the different GM1-AmB preparations, and their respective controls, was incubated with 900 ul *candida Albicans* solution at a concentration of $1\times10^5$ cells/ml on a plate of 96 wells for 24 hours at 37° C. Serial dilutions were made on the plate to a final concentration of AmB 0.0625 ug/ml. After incubation, the turbidity of the solution, which represents the growth of the micro-organism, was evaluated by spectrophotometry at 610 nm. FIG. 15 shows that GM1-AmB complex to a ratio 1:5 produces a cell growth inhibition equal to that seen in the AmB control. On the other hand, 1:2.5 and 1:1 ratios produce a growth inhibition just

The invention claimed is:

1. A water soluble pharmaceutical composition, comprising at least one therapeutically active hydrophobic substance and at least one compound selected from the group consisting of sialoglycosphingolipids and a mixture of sialoglycosphingolipids and glycosphingolipids, wherein said at least one therapeutically active substance is an antitumor drug or an antimycotic drug and said drug is non-covalently bound to said at least one compound to form nanomicelles wherein said nanomicelles form a complex with a plasma protein, wherein the drug and at least one compound are present in the composition at a molar ratio of 1:10 and 1:100.

2. The water soluble pharmaceutical composition according to claim 1, wherein said at least one compound is selected from sialoglycosphingolipids.

3. The water soluble pharmaceutical composition according to claim 1, wherein said plasma protein is albumin.

4. The water soluble pharmaceutical composition according to claim 1, wherein the glycosphingolipids are gangliosides.

5. The water soluble pharmaceutical composition according to claim 4, wherein the gangliosides are monosialogangliosides, disialogangliosides, trisialogangliosides or a mixture thereof.

6. The water soluble pharmaceutical composition according to claim 4, wherein said drug is paclitaxel.

7. The water soluble pharmaceutical composition according to claim 4, wherein said drug is docetaxel.

8. The water soluble pharmaceutical composition according to claim 6, comprising between 0.1 mg/ml to 6 mg/ml of paclitaxel or docetaxel and between 4 mg/ml and 300 mg/ml of gangliosides.

9. The water soluble pharmaceutical composition according to claim 1, wherein the nanomicelles are, on average, between 10 nm and smaller than 100 nm.

10. The water soluble pharmaceutical composition according to claim 9, wherein the nanomicelles are, on average, between 20 nm and 60 nm.

11. A water soluble pharmaceutical composition, comprising at least one therapeutically active hydrophobic substance and at least one compound selected from the group consisting of sialoglycosphingolipids and a mixture of sialoglycosphingolipids and glycosphingolipids, wherein said at least one therapeutically active substance is doxorubicin and said doxorubicin is non-covalently bound to said at least one compound to form nanomicelles wherein said nanomicelles form a complex with a plasma protein,
wherein the drug and at least one compound are present in the composition at a molar ratio of 1:1 and 1:50.

12. The water soluble pharmaceutical composition according to claim 4 comprising doxorubicin and paclitaxel or docetaxel as the at least one therapeutically active substance, at a drug:ganglioside molar ratio for each of the drug present of between 1:10 and 1:100.

13. A water soluble pharmaceutical composition, comprising at least one therapeutically active hydrophobic substance and at least one compound selected from the group consisting of sialoglycosphingolipids and a mixture of sialoglycosphingolipids and glycosphingolipids, wherein said at least one therapeutically active substance is amphotericin B and said amphotericin B is non-covalently bound to said at least one compound to form nanomicelles wherein said nanomicelles form a complex with a plasma protein,
wherein the drug and at least one compound are present in the composition at a molar ratio of 2:1 and 1:5.

14. The water soluble pharmaceutical composition according to claim 13, comprising amphotericin B at an amphotericin B:ganglioside molar ratio of 1:1.

15. The water soluble pharmaceutical composition according to claim 14, comprising between 0.1 mg/ml and 10 mg/ml amphotericin B and between 0.18 mg/ml and 10 mg/ml gangliosides.

16. The water soluble pharmaceutical composition according to claim 1, wherein the average size of the nanomicelles is between 10 nm and less than 200 nm.

17. The water soluble pharmaceutical composition according to claim 1 wherein, the average size of the nanomicelles is in the range of 20 nm and 80 nm.

18. The water soluble pharmaceutical composition according to claim 4, wherein the ganglioside nanomicelles are non-covalently coated with human serum albumin, recombinant human serum albumin or bovine albumin.

19. The water soluble pharmaceutical composition according to claim 18, wherein the ganglioside nanomicelles are non-covalently coated with human serum albumin.

20. The water soluble pharmaceutical composition according to claim 18, wherein the ganglioside nanomicelles are coated with albumin containing covalently bound folic acid.

21. A water soluble pharmaceutical composition, comprising at least one therapeutically active hydrophobic substance and at least one compound selected from the group consisting of sialoglycosphingolipids and a mixture of sialoglycosphingolipids and glycosphingolipids, wherein said at least one therapeutically active substance is a drug selected from the group consisting of a prostaglandin, isosorbide dinitrate, testosterone, nitroglycerin, estradiol, vitamin E, cortisone, dexamethasone, an ester of dexamethasone and betamethasone valerate, and said drug is non-covalently bound to said at least one compound to form nanomicelles wherein said nanomicelles form a complex with a plasma protein,
wherein the drug and at least one compound are present in the composition at a molar ratio of 1:10 and 1:100.

22. A method for obtaining nanomicelles according to claim 1, containing at least one therapeutically active nanoencapsulated substance, comprising:
(a) solubilizing gangliosides in distilled water or saline solution with a pH ranging between 3 and 7, always above the critical nanomicelle concentration, and allowing the solution to stand;
(b) adding 10% dimethylsulphoxide or ethanol solution containing the selected therapeutically active substance to the ganglioside nanomicelle solution obtained according to the previous stage;
(c) incubating the mixture in order to ensure the right incorporation of the therapeutically active substance into the micelles;
(d) dialyzing the micellar solution containing the therapeutically active substance in a distilled water solution or a pharmaceutically acceptable solution with a pH comprised between 3 and 7, in order to remove the organic solvent completely;
(e) incubating the nanomicelles composed of the GM1-therapeutically active substance complex in the presence of human serum albumin in order to allow the formation of the ternary GM1—therapeutically active substance—albumin complex;
(f) sterilizing the aqueous and transparent solution obtained in the previous stage, which contains the therapeutically active substance incorporated into the GM1 micelle by means of filtration;
(g) lyophilizing the sterilized nanomicelles and, finally,
(h) resuspending the lyophilized nanomicelles in a pharmaceutically acceptable solution.

* * * * *